(12) United States Patent
Mach et al.

(10) Patent No.: US 7,947,838 B2
(45) Date of Patent: May 24, 2011

(54) RADIOLABELLED BENZAMIDE ANALOGUES, THEIR SYNTHESIS AND USE IN DIAGNOSTIC IMAGING

(75) Inventors: Robert Mach, Eureka, MO (US); Zhude Tu, Frontenac, MO (US)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 12/643,175

(22) Filed: Dec. 21, 2009

(65) Prior Publication Data
US 2010/0150836 A1  Jun. 17, 2010

Related U.S. Application Data

(60) Division of application No. 11/757,246, filed on Jun. 1, 2007, now Pat. No. 7,659,400, which is a continuation-in-part of application No. 10/903,771, filed on Jul. 30, 2004, now Pat. No. 7,390,902.

(60) Provisional application No. 60/491,582, filed on Jul. 31, 2003.

(51) Int. Cl.
*C07D 451/00* (2006.01)
*C07D 451/14* (2006.01)

(52) U.S. Cl. ............................................ 546/86; 546/87

(58) Field of Classification Search ................. 546/86, 546/87; 424/1.85, 1.81
See application file for complete search history.

(56) References Cited

U.S. PATENT DOCUMENTS

| | | | |
|---|---|---|---|
| 4,197,243 A | 4/1980 | Murakami et al. | |
| 5,294,621 A | 3/1994 | Russell | |
| 6,046,210 A | 4/2000 | Stemp et al. | |
| 6,113,877 A | 9/2000 | Mach et al. | |
| 6,447,748 B1 | 9/2002 | John et al. | |
| 7,659,400 B2 * | 2/2010 | Mach et al. | 546/86 |
| 2005/0107398 A1 | 5/2005 | Mach et al. | |
| 2008/0161343 A1 | 7/2008 | Mach et al. | |

FOREIGN PATENT DOCUMENTS

| | | |
|---|---|---|
| JP | 8-510235 | 10/1996 |
| JP | 11-503754 | 3/1999 |
| JP | 2001-502683 | 2/2001 |
| WO | 94/26314 | 11/1994 |
| WO | 96/32968 | 10/1996 |
| WO | 98/17648 | 4/1998 |
| WO | 2005048810 | 6/2005 |

OTHER PUBLICATIONS

International Search Report in the related application PCT/US08/655555 issued on Mar. 3, 2009.
Supplementary Partial European Search Report issued on Oct. 10, 2008, in related application 04817745.5.
Curtet et al, New arylpiperazine derivatives as antagonists of the human cloned 5-HT4 receptor isoforms, J Med Chem, 2000, 43:3761-3769.
Hackling et al, N-(omega-(4-(2-methoxyphenyl)piperazin-1-yl)alkyl)carboxamides as dopamine D2 and D3 receptor ligands, J Med Chem, 2003, 46:3883-3899.
Leopoldo et al, Structure-affinity relationship study on N-[4-(4-arylpiperazin-1-yl)butyl]aryl carboxamides as potent and selective dopamine D3 receptor ligands, J Med Chem, 2002, 45:5727-5735.
International Report on Patentability issued Feb. 6, 2006, in the related application PCT/US04/25304.
Al-Nabulsi I, et al., Effect of ploidy, recruitment, environmental factors, and tamoxifen treatment on the expression of sigma-2 receptors in proliferating and quiescent tumour cells, Br. J. Cancer, 1999, p. 925-933, vol. 81(6).
Anderson CJ and Welch MJ, Radiometal-labeled agents (non-technetium) for diagnostic imaging, Chem. Rev., 1999, p. 2219-2234, vol. 99(9).
Berardi F, et al., 4-(tetralin-1-yl)- and 4-(naphthalen-1-yl)alkyl derivatives of 1-cyclohexylpiperazine as sigma receptor ligands with agonist sigma2 activity, J. Med. Chem., 2004, p. 2308-2317, vol. 47(9).
Bonhaus DW, et al., [3H]BIMU-1, a 5-hydroxytryptamine3 receptor ligand in NG-108 cells, selectively labels sigma-2 binding sites in guinea pig hippocampus, J. Pharmacol. Exp. Ther., 1993, p. 961-970, vol. 267(2).
Bowen WD, et al., Ibogaine and its congeners are sigma 2 receptor-selective ligands with moderate affinity, Eur. J. Pharmacol., 1995, p. 257-260, vol. 278(3).
Colabufo NA, et al., Distribution of sigma receptors in EMT-6 cells: preliminary biological evaluation of PB167 and potential for in-vivo PET, J. Pharm. Pharmacol., 2005, p. 1453-1459, vol. 57(11).
Hou C, et al., Characterization of a novel iodinated sigma-2 receptor ligand as a cell proliferation marker, Nucl. Med. Biol., 2006, p. 203-209, vol. 33(2).
Huang Y, et al., Synthesis and structure-activity relationships of naphthamides as dopamine D3 receptor ligands, J. Med. Chem., 2001, p. 1815-1826, vol. 44(11).
Jurisson SS and Lydon JD, Potential technetium small molecule radiopharmaceuticals, Chem. Rev., 1999, p. 2205-2218, vol. 99(9).
Kassiou M, et al., Synthesis and in vivo evaluation of a new PET radioligand for studying sigma-2 receptors, Bioorg. Med. Chem., 2005, p. 3623-3626, vol. 13(11).
Laforest R, et al., MicroPET imaging with nonconventional isotopes, IEEE Transactions on Nuclear Science, 2002, p. 2119-2126, vol. 49(5).
Mach RH, et al., Sigma 2 receptors as potential biomarkers of proliferation in breast cancer, Cancer Res., 1997, p. 156-161, vol. 57(1).
Mach RH, et al., Synthesis of 2-(5-bromo-2,3-dimethoxyphenyl)-5-(aminomethyl)-1H-pyrrole analogues and their binding affinities for dopamine D2, D3, and D4 receptors, Bioorg. Med. Chem., 2003, p. 225-233, vol. 11(2).
Mach RH, et al., [[(18)F]N-(4'-fluorobenzyl)-4-(3-bromophenyl) acetamide for imaging the sigma receptor status of tumors: comparison with [(18)F]FDG, and [(125)I]IUDR, Nucl. Med. Biol., 2001, p. 451-458, vol. 28(4).

(Continued)

*Primary Examiner* — Nizal S Chandrakumar
(74) *Attorney, Agent, or Firm* — Zackson Law LLC; Saul L. Zackson

(57) ABSTRACT

Fluoroalkoxybenzamide compounds which selectively bind Sigma-2 receptors are disclosed. These compounds, when labelled with $^{18}$F, can be used as radiotracers for imaging of tumors by positron emission tomography (PET). In addition, these compounds, when labelled with $^{123}$I, can be used as radiotracers for imaging of tumors by single photon emission computed tomography (SPECT). Methods for synthesis of these compounds are also disclosed.

8 Claims, 10 Drawing Sheets

OTHER PUBLICATIONS

Mach RH, et al., Conformationally-flexible benzamide analogues as dopamine D3 and sigma 2 receptor ligands, Bioorg. Med. Chem. Lett, 2004, p. 195-202, vol. 14(1).

Tu Z, et al., Carbon-11 labeled sigma2 receptor ligands for imaging breast cancer, Nucl. Med. Biol., 2005, p. 423-430, vol. 32(5).

Wheeler KT, et al., Sigma-2 receptors as a biomarker of proliferation in solid tumours, Br. J. Cancer, 2000, p. 1223-1232, vol. 82(6).

Xu J, et al., [3H]N-[4-(3,4-dihydro-6,7-dimethoxyisoquinolin-2(1H)-yl)butyl]-2-methoxy-5-methylbenzamide: a novel sigma-2 receptor probe, Eur. J. Pharmacol., 2005, p. 8-17, vol. 525(1-3).

Notification of the First Office Action issued on Dec. 24, 2010, in connection with Japanese Application No. 2006-522145 (Japanese language).

Notification of the First Office Action issued on Dec. 24, 2010, in connection with Japanese Application No. 2006-522145 (English translation).

Anderson A., et al., J. Med. Chem, 44: 3582-3591, 2001.

S. Curtet et al.: New aryl piperazine derivatives as antagonists of the human cloned 5-ht4 receptor isoforms, Journal of Medicinal Chemistry vol. 43, No. 20, 2000, pp. 3761-3769, American Chemical Society, Washington, DC, US.

Leopoldo M et al: Structure-affinity relationship study on N-[4-(4-arylpiperazin-1-yl)butyl]arylcarboxamides as potent and selective dopamine D3 receptor ligands, Journal of Medicinal Chemistry vol. 45, No. 26, 2002, pp. 5727-5735, American Chemical Society, Washington, DC, US.

Hackling. A., et al: N-(ω-(4-(2-Methoxyphenyl) piperazin-1-yl)alkyl)carboxamides as Dopamine D2 and D3 receptor ligands. Journal of Medicinal Chemistry vol. 46, No. 18, 2003, pp. 3863-3899, American Chemical Society, Washington, DC, US.

Mach, R, et al.: Conformationally-flexible benzamide analogues as dopamine 03 and sigma2 receptor ligands, Bioorganic & Medicinal Chemistry Letters vol. 14, No. 1, pp. 195-202, Elsevier, Inc., New York, NY, US.

* cited by examiner

Reagents: (a) RCOOH, BOP/CH$_2$Cl$_2$ or DCC / CH$_2$Cl$_2$, rt, 18 hrs; (b) BrCH$_2$CH$_2$F, K$_2$CO$_3$/acetone reflux, over 48hrs; (c)[Sn(C$_4$H$_9$)$_3$]$_2$ , Pd(PPh$_3$)$_4$(0) / toluene at 110°C; (d) I$_2$ / CH$_2$Cl$_2$, room temperature;

Scheme I

Reagent: (a) BrCH₂CH₂OAc/acetone, K₂CO₃, reflux 18 hrs; (b) NaOH / H₂O, CH₃OH, room temperature; (c) methanesulfonyl chloride, CH₂Cl₂, triethylamine, room temperature.

Scheme II.

Reagents: (a) Methanol / 98% H$_2$SO$_4$ reflux 18 hrs; (b) BrCH$_2$CH$_2$OAc/acetone, K$_2$CO$_3$, reflux 18 hrs; (c) [Sn(C$_4$H$_9$)$_3$]$_2$ , Pd(PPh$_3$)$_4$(0) / toluene at 110°C; (d) I$_2$ / CH$_2$Cl$_2$, room temperature; (e) NaOH / H$_2$O, CH$_3$OH, room tempearture; (f) 1b, BOP/CH$_2$Cl$_2$ or DCC / CH$_2$Cl$_2$, room temperature, 18 hrs; (g) methanesulfonyl chloride, CH$_2$Cl$_2$, triethylamine, room temperature, 18hrs.

Scheme III.

Scheme IV.

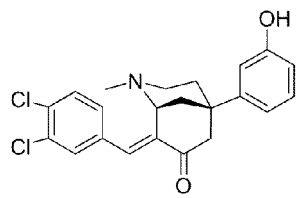

10
$\sigma_1$ = 7436 ± 308 nM
$\sigma_2$ = 13.4 ± 2.0 nM
$\sigma_1 : \sigma_2$ ratio = 554
LogP = 3.84 (pH = 7.4)

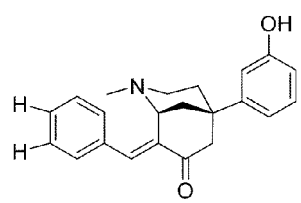

11
$\sigma_1$ = 3,063 ± 78 nM
$\sigma_2$ = 16.5 ± 2.7 nM
$\sigma_1 : \sigma_2$ ratio = 185
LogP = 3.84 (pH = 7.4)

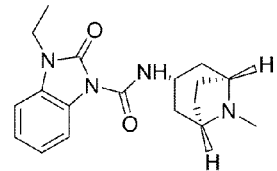

12
$\sigma_1$ = 6,300 nM
$\sigma_2$ = 32 nM
$\sigma_1 : \sigma_2$ ratio = 200
LogP = -0.96 (pH = 7.4)

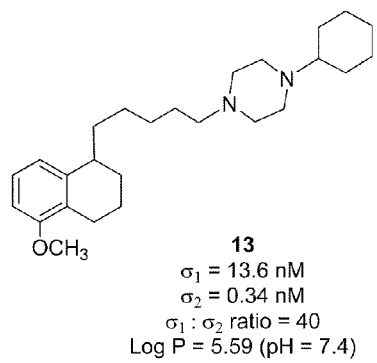

13
$\sigma_1$ = 13.6 nM
$\sigma_2$ = 0.34 nM
$\sigma_1 : \sigma_2$ ratio = 40
Log P = 5.59 (pH = 7.4)

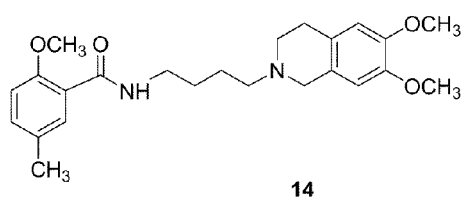

14
$\sigma_1$ = 3078 ± 87 nM
$\sigma_2$ = 10.3 ± 1.5 nM
$\sigma_1 : \sigma_2$ ratio = 299
Log P = 2.83 (pH = 7.4)

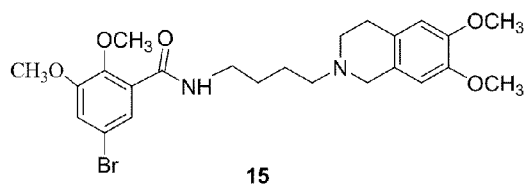

15
$\sigma_1$ = 12,900 ± 111 nM
$\sigma_2$ = 8.2 ± 1.4 nM
$\sigma_1 : \sigma_2$ ratio = 1575
Log P = 3.3 (pH = 7.4)

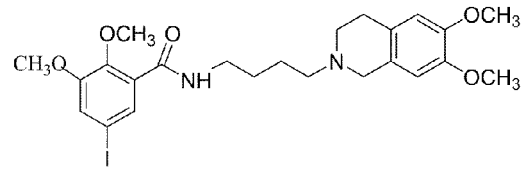

16
$\sigma_1$ = 554 nM
$\sigma_2$ = 11 nM
$\sigma_1 : \sigma_2$ ratio = 50
Log P = 3.94 (pH = 7.4)

FIG. 5

RADIOLABELLED BENZAMIDE ANALOGUES, THEIR SYNTHESIS AND USE IN DIAGNOSTIC IMAGING

RELATED APPLICATIONS

The present application is a divisional of U.S. patent application Ser. No. 11/757,246, filed Jun. 1, 2007, now patented, which is a continuation-in-part of U.S. patent application Ser. No. 10/903,771 filed Jul. 30, 2004, now patented, which claims priority to U.S. Provisional Application 60/491,582 filed Jul. 31, 2003. These applications are hereby incorporated by reference in their entireties.

INTRODUCTION

Sigma receptors are a class of receptors that are expressed in many normal tissues, including liver, kidneys, endocrine glands, and the central nervous system (CNS) (Walker, J. M., et al. Pharmacol Rev 42: 355-402 1990). It has been well established that there are at least two types of sigma receptors, sigma-1 ($\sigma_1$) and sigma-2 ($\sigma_2$) (Walker, J. M., et al. Pharmacol Rev 42, 355-402, 1990). Overexpression of $\sigma_2$ receptors has been reported in a variety of human and murine tumors (Bem, W. T., et al., Cancer Res 51: 6558-6562, 1991; Vilner, B. J., et al., In: Multiple sigma and PCP receptor ligands: mechanisms for neuromodulation and neuroprotection?, Kamenka, J. M., and Domino, E. F., ed, Ann Arbor (Mich), 7 NPP Books, p. 341-353, 1992; Mach, R. H., et al., Cancer Res. 57: 156-161, 1997).

Searches for $\sigma_2$ selective ligands has led to the identification of a number compounds having modest to high selectivity for $\sigma_2$ versus $\sigma_1$ receptors (FIG. 5). These include CB-184 (10), CB-64D (11), BIMU-1 (12) (Bowen, W. D., et al., Eur. J. Pharmacol. 278: 257-260, 1995; Bonhaus, D. W., et al., J. Pharmacol. Exp. Ther. 267: 96, 1993). and PB-167 (13) (Colabufo, N. A., et al., J. Pharmacy and Pharmacology 57: 1453-1459, 2005; Kassiou, M., et al., Bioorganic and Medicinal Chemistry, 13: 3623-3626, 2005; Berardi, F., et al., J. Med. Chem. 2004, 47: 2308-2317) as well as certain benzamide analogs (14-16) (Mach, R. H., et al., Bioorg. Med. Chem. 11: 225, 2003; Huang, Y., et al., J. Med. Chem. 44: 1815, 2001; U.S. patent application Ser. No. 10/903,771 to Mach et al). We previously reported the evaluation of several $^{11}$C, $^{76}$Br and $^{125/123}$I radiolabelled conformationally-flexible benzamide analogs using EMT-6 tumor-bearing female Balb/c mice (Tu, Z., et al., Nucl. Med. Biol. 32: 423-430, 2005; Xu, J., et al., Eur. J. Pharmacol. 21: 525 (1-3): 8-17, 2005; Hou, C., et al., Nucl. Med. Biol. February, 33: 203-9, 2006). Initial in vivo studies of 5-methyl-2-[$^{11}$C]-methoxy-N-[2-(6,7-dimethoxy-3,4-dihydro-1H-isoquinolin-2-yl)-butyl]-benzamide and 5-[$^{76}$Br]-bromo-2,3-dimethoxy-N-[2-(6,7-dimethoxy-3,4-dihydro-1H-isoquinolin-2-yl)-butyl]-benzamide indicated that these compounds were potential radiopharmaceuticals for imaging solid tumors and their proliferative status with positron emission tomography (PET). However, the radionuclide properties of $^{76}$Br and $^{11}$C make these isotopes less than ideal for PET imaging. For example, images produced by PET using $^{76}$Br as a radiotracer are often blurry, (Laforest. R., et al., IEEE Transactions on Nuclear Science, 49: 2119-2126, 2002), and the short half-life of $^{11}$C ($t_{1/2}$=20.4 min) places time constraints on tracer synthesis and duration of scan sessions. Contrast between tumor and normal tissues can be less than satisfactory when a $\sigma_2$-selective radiotracer tagged with $^{11}$C is used in PET imaging. Accordingly, alternative $\sigma_2$-selective ligands for use as radiotracers in PET imaging are needed.

SUMMARY

The present inventors have developed a series of compounds which can be used as radiolabels for diagnostic imaging, in particular positron emission tomography (PET) imaging of tumors. The compounds selectively bind Sigma receptors, and in particular bind Sigma-2 receptors in preference to Sigma-1 receptors. The compounds also selectively bind to tumor cells, and thus can also be used as tracers for detecting tumor cells. In addition, because in some embodiments, the compounds comprise the radioisotope $^{18}$F, they can be used as radiotracers for imaging tumors using PET.

In some embodiments, a tracer the present teachings is a fluoroalkoxybenzamide compound having a structure

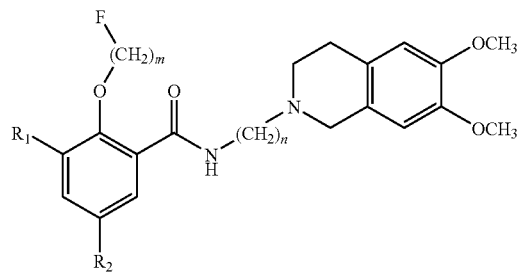

wherein m is an integer from 1 to about 10, n is an integer from 1 to about 10, and $R_1$ and $R_2$ are each independently selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$, or a salt thereof.

In some embodiments, a compound of the present teachings can include at least one $^{18}$F isotope. A compound of these embodiments can be a radiolabelled fluoroalkoxybenzamide compound having a structure

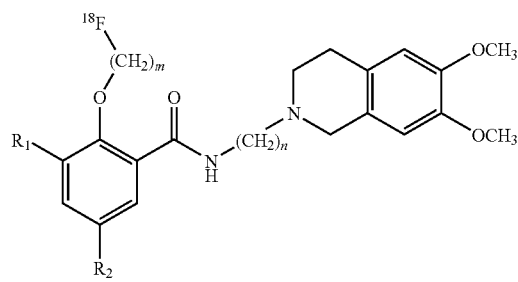

wherein m is an integer from 1 to about 10, n is an integer from 1 to about 10, and $R_1$ and $R_2$ are each independently selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$, or a salt thereof.

Other embodiments of the present teachings include methods of synthesizing a fluoroalkoxybenzamide compound of structure

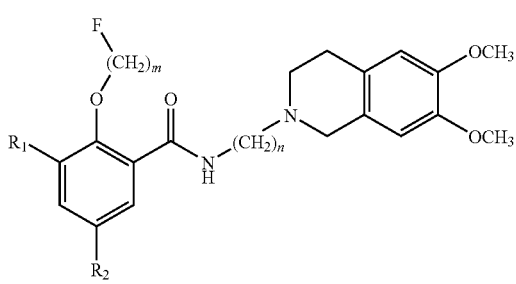

These methods comprise reacting a compound of structure

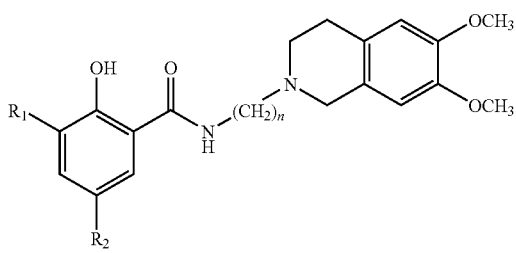

with an fluorinated compound such as

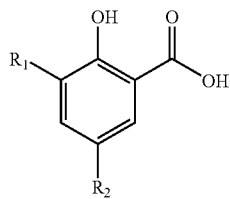

wherein m is an integer from 1 to about 10, n is an integer from 1 to about 10, and $R_1$ and $R_2$ are each independently selected from the group consisting of H, a halogen selected from the group consisting of Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$. In some aspects of these embodiments, m can be 2, n can be 2, $R_1$ can be H, and $R_2$ can be $CH_3$. In some aspects, these methods can further comprise reacting

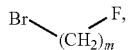

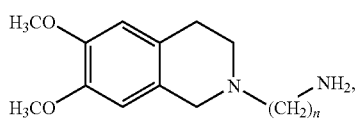

thereby forming

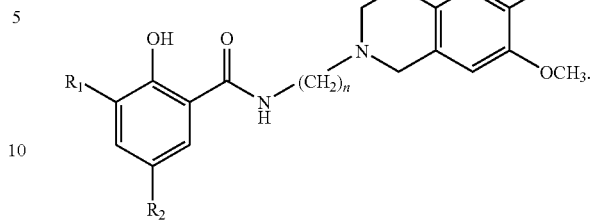

In other aspects, m can be 2, n can be 4, $R_1$ can be selected from the group consisting of $OCH_3$ and H, and $R_2$ can be selected from the group consisting of Br, $CH_3$, and I. In yet other aspects, m=2, n=4, $R_1$ is H, and $R_2$ is I.

In yet other embodiments of the present teachings, the inventors disclose methods for synthesizing radiolabelled fluoroalkoxybenzamide compounds of structure

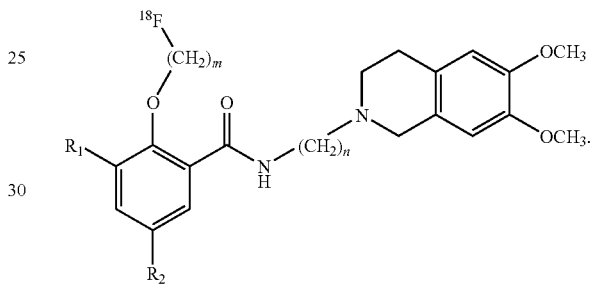

These methods comprise forming a mixture comprising i) an organic solvent, ii) a compound of structure

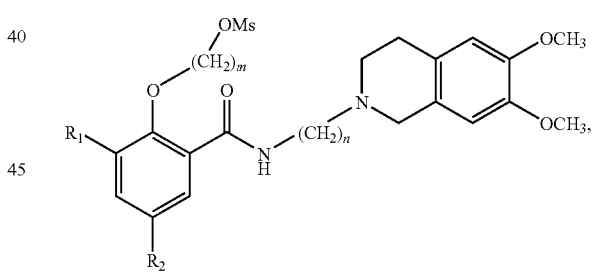

iii) $^{18}F^-$, iv) 4,7,13,16,21,24-Hexaoxa-1,10-diazabicyclo[8.8.8]-hexacosane and v) a potassium salt, wherein m is an integer from 1 to about 10, n is an integer from 1 to about 10, $R_1$ and $R_2$ are each independently selected from the group consisting of H, a halogen selected from the group consisting of Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$. In some aspects of these methods, m can be 2, n can be 4, $R_1$ can be selected from the group consisting of H and $OCH_3$, and $R_2$ can be selected from the group consisting of $CH_3$, Br and I. In yet other aspects of these methods, m=2, n=4, $R_1$ is $OCH_3$, and $R_2$ is I. In addition, in various aspects, the potassium salt can be $K_2CO_3$, and the organic solvent can be dimethyl sulfoxide, acetonitrile or a combination thereof. Furthermore, in various aspects, the methods can include heating a mixture.

In additional embodiments of the present teachings, the inventors disclose methods of imaging a tumor in a mammal such as a human. These methods comprise administering to the mammal a radiolabelled fluoroalkoxybenzamide compound of structure

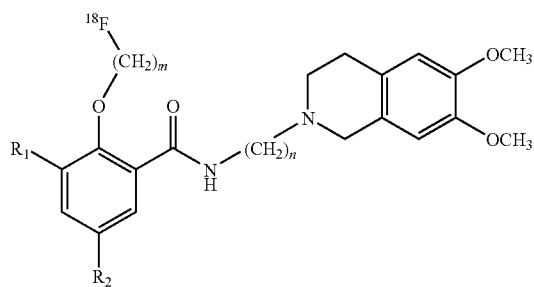

wherein m is an integer from 1 to about 10, n is an integer from 1 to about 10, and $R_1$ and $R_2$ are each independently selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$, or a salt thereof; and subjecting the mammal to positron emission tomography (PET) scanning. In some aspects, m can be 2, n can be 4, $R_1$ can be selected from the group consisting of H and $OCH_3$, and $R_2$ can be selected from the group consisting of $CH_3$, Br and I.

In various aspects of the above embodiments, a fluoroalkoxybenzamide compound or a salt thereof can include particular molecular species, such as,

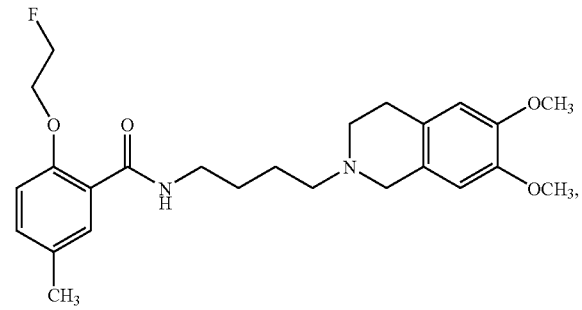

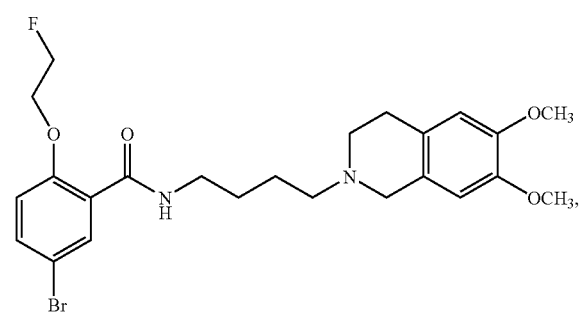

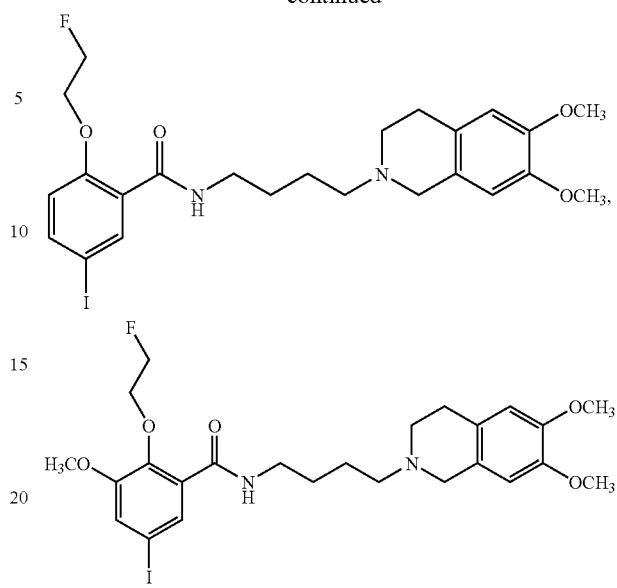

or salts thereof.

In various aspects of these embodiments, a radiolabelled fluoroalkoxybenzamide compound or a salt thereof can include particular molecular species, such as,

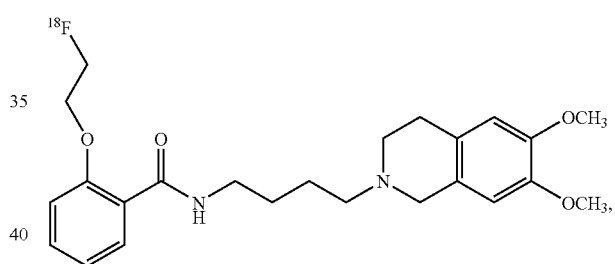

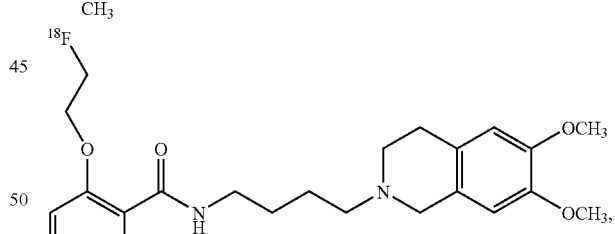

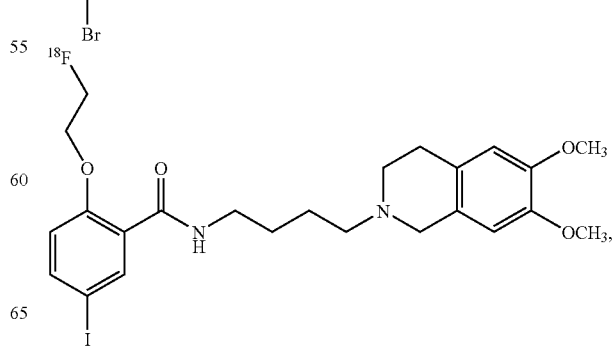

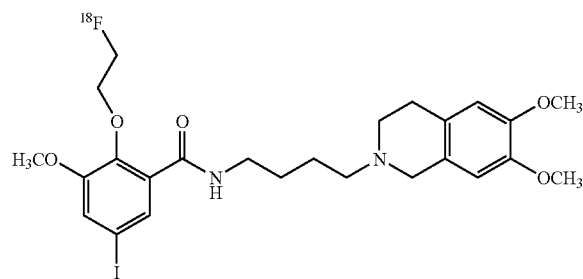

or salts thereof.

In additional embodiments of the present teachings, the inventors disclose methods for synthesizing compounds of structure

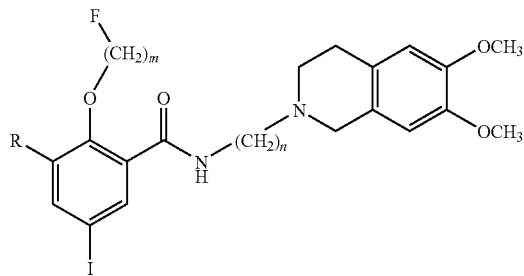

wherein m is an integer from 1 to about 10, n is an integer from 1 to about 10, and R is H or a $C_{1-4}$ alkoxy such as a methoxy. These methods comprise:

stannylating a compound of structure

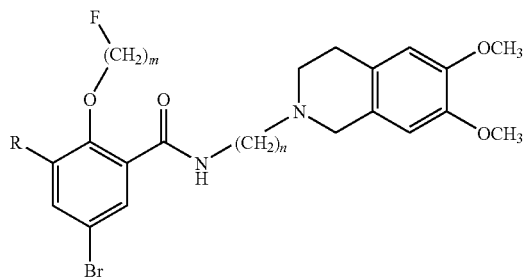

to form a compound of structure

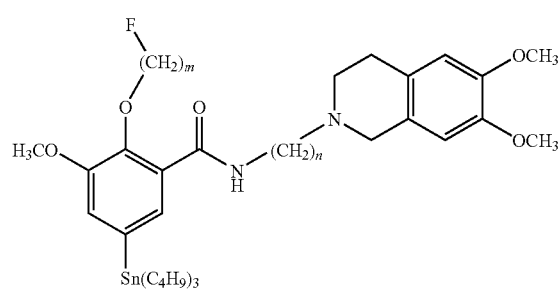

and iodinating a compound of structure

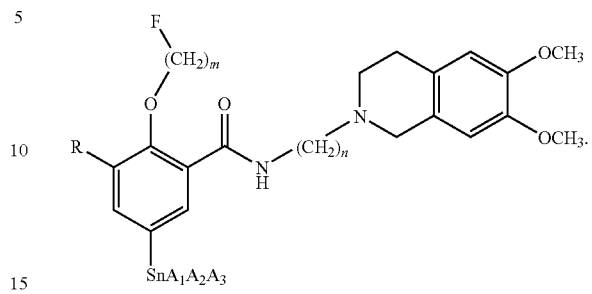

In some configurations, the stannylated compound can be formed by stannylating a compound of structure

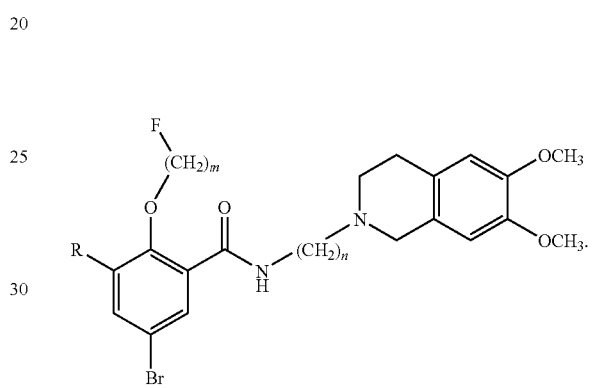

In some aspects of these methods, m can be 2 and n can be 4.

In yet other embodiments of the present teachings, the inventors disclose iodine-123 radiolabelled fluoroalkoxybenzamide compounds of structure

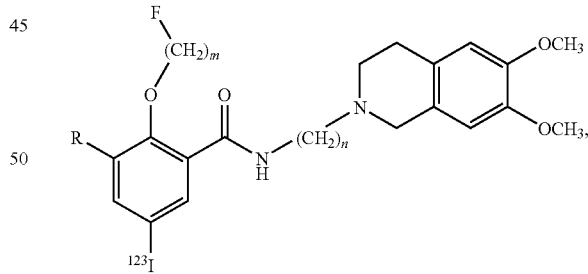

wherein m is an integer from 1 to about 10, n is an integer from 1 to about 10, and R can be H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$, and salts thereof. In various configurations, m can be 2, n can be 4, R can be H or a $C_{1-4}$ alkoxy such as a methoxy.

In related embodiments, the inventors disclose methods for synthesizing these radioiodinated compounds. In various configurations, these methods include reacting a compound of structure

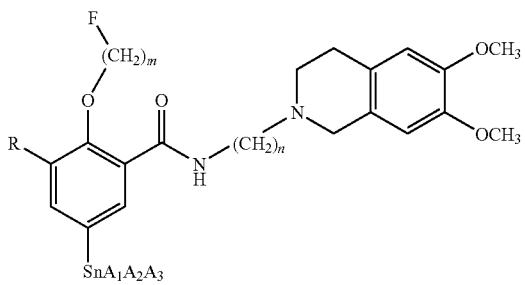

with [$^{123}$I]NaI and an oxidant, wherein m is an integer from 1 to about 10, n is an integer from 1 to about 10, $A_1$, $A_2$ and $A_3$ are each independently a $C_{1-4}$ alkyl, and R is selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$. In various aspects, R can be H or a $C_{1-4}$ alkoxy such as a methoxy; $A_1$, $A_2$ and $A_3$ can each be independently a butyl moiety selected from an n-butyl moiety, an iso-butyl moiety, a sec-butyl moiety, and a tert-butyl moiety. In some configurations, $A_1$, $A_2$ and $A_3$ can each be an n-butyl moiety, m can be 2 and n can be 4. In addition, in various aspects, the oxidant can be peracetic acid, hydrogen peroxide, chloramine T (N-chloro-p-toluenesulfonamide sodium salt) or a combination thereof.

In some aspects of these embodiments, the methods can further include stannylating a compound of structure

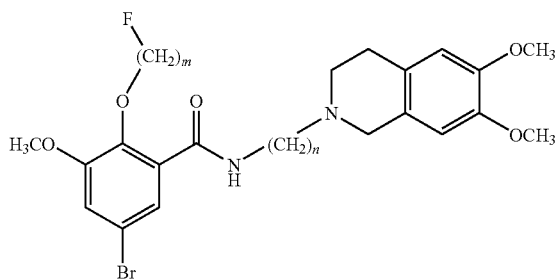

to form a compound of structure

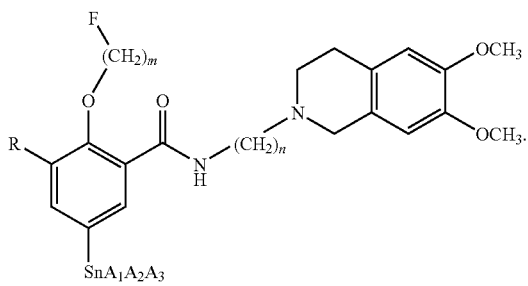

In yet other embodiments, the present teachings include methods of imaging a solid tumor in a mammal such as a human. In various configurations, these methods include administering to the mammal a radioiodinated compound described above, and subjecting the mammal to single photon emission computed tomography (SPECT) imaging.

BRIEF DESCRIPTION OF THE DRAWINGS

FIG. 5 illustrates structure and properties of several $\sigma_2$ selective ligands.

DETAILED DESCRIPTION

Figure 1:
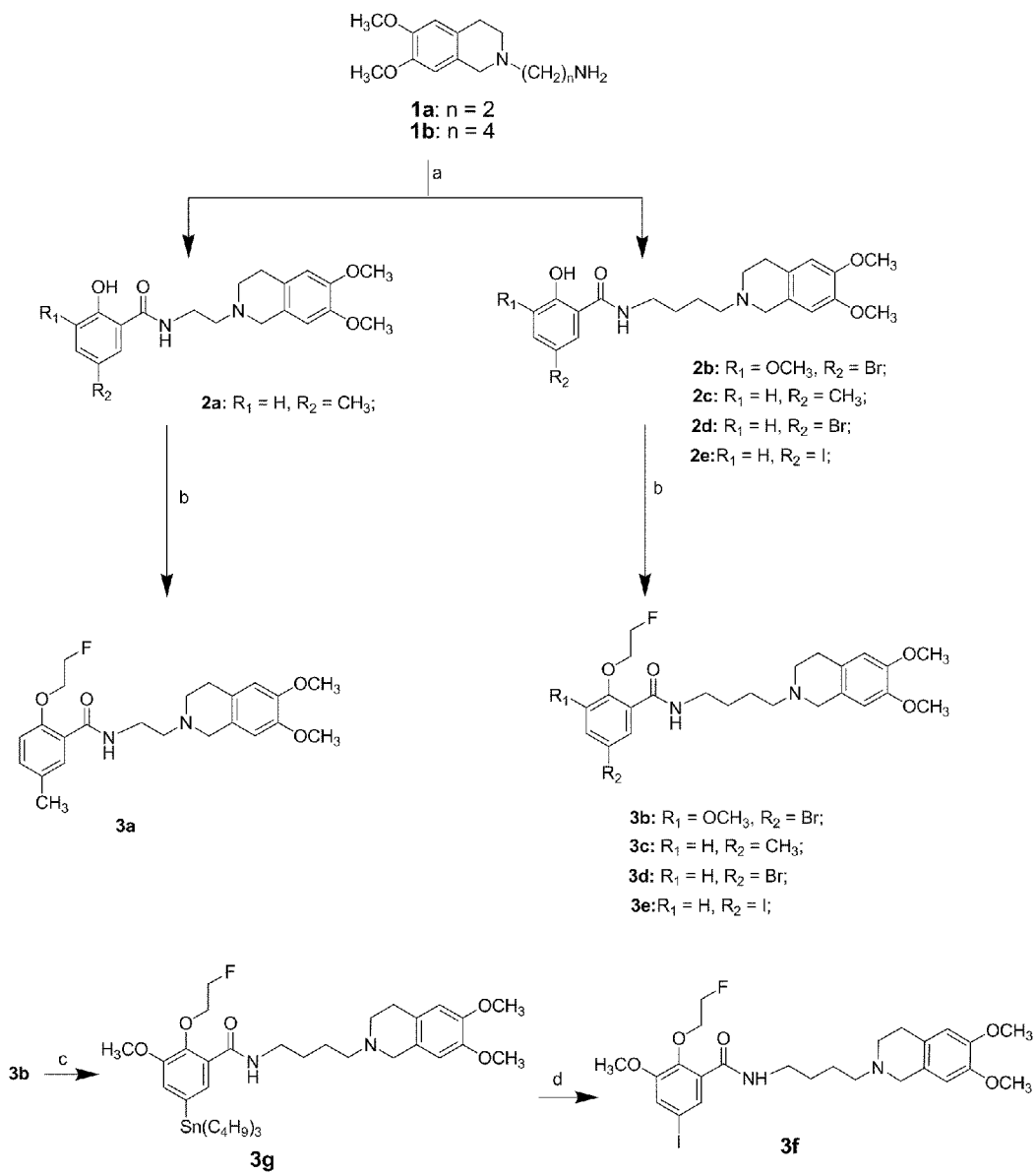
FIG. 1 illustrates scheme I for synthesis of some compounds of the present teachings.

The present inventors have developed a series of compounds which can be used as radiolabels for diagnostic imaging, in particular positron emission tomography (PET) imaging of tumors. The compounds selectively bind Sigma receptors, and in particular bind Sigma-2 receptors in preference to Sigma-1 receptors. The compounds also selectively bind to tumor cells, and thus can be used as tracers for detecting tumor cells. Without being limited by theory, it is generally believed that many types of tumor cells have a high density of sigma-2 receptors, and therefore compounds of the present teachings are effective tracers for detecting tumors by virtue of the compounds' affinity for the sigma-2 receptors. In addition, because in some embodiments, the compounds comprise the radioisotope $^{18}$F, a preferred isotope for imaging by positron emission tomography (PET) they are effective as radiotracers for PET imaging of tumors in humans or other mammals. Furthermore, in some embodiments, the compounds comprise the radioisotope $^{123}$I, a preferred isotope for imaging by single photon emission computed tomography (SPECT). These compounds are effective as radiotracers for SPECT imaging of tumors in humans or other mammals.

The present inventors have synthesized several novel conformationally flexible benzamide analogues having a moderate to high binding affinity and selectivity for $\sigma_2$ receptors (Table I). Four of these compounds were selected as candidates for developing $^{18}$F-labeled PET [$^{18}$F]3c, [$^{18}$F]3d, probes to image the $\sigma_2$ receptor status of solid tumors. [$^{18}$F] 3c, [$^{18}$F]3d, [$^{18}$F]3e, and [$^{18}$F]3f, were successfully synthesized and evaluated as potential radiotracers for imaging EMT-6 tumors in female Balb/c mice. Of the four $^{18}$F-labeled analogues, [$^{18}$F]3c and [$^{18}$F]3f had the best biodistribution kinetics and tumor:normal tissue ratios. Blocking studies confirmed that the uptake of [$^{18}$F]3c and [$^{18}$F]3f was $\sigma_2$-receptor mediated. Our studies indicate that various compounds of the present teachings, including [$^{18}$F]3c and [$^{18}$F]3f, are acceptable agents for detecting and imaging solid tumors and their $\sigma_2$ receptor status with PET.

The present inventors devised a design strategy for generating $\sigma_2$-selective ligands of the present teachings. This strategy involved replacing the ortho methoxy group of $^{11}$C-labelled benzamide analogs (Xu, J., et al., Eur. J. Pharmacol. 21; 525 (1-3): 8-17, 2005) with a 2-fluoroethyl group as shown in Scheme I (FIG. 1) and in Examples below.

The following examples are illustrative of the various embodiments of the present teachings. The examples are not intended to limit the scope of the claims. The methods described herein utilize laboratory techniques well known to skilled artisans, and guidance can be found in laboratory manuals and textbooks such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999; Hedrickson et al., Organic Chemistry 3rd edition, McGraw Hill, New York, 1970; Carruthers, W., and Coldham, I., Modern Methods of Organic Synthesis (4th Edition), Cambridge University Press, Cambridge, U.K., 2004; Curati, W. L., Imaging in Oncology, Cambridge University Press, Cambridge, U.K., 1998; Welch, M. J., and Redvanly, C. S., eds. Handbook of Radiopharmaceuticals: Radiochemistry and Applications, J. Wiley, New York, 2003.

In the experiments described in herein, all reagents were purchased from commercial suppliers and used without further purification unless otherwise stated. Tetrahydrofuran (THF) was distilled from sodium hydride immediately prior to use Anhydrous toluene was distilled from sodium/toluene shortly before use. All anhydrous reactions were carried out in oven-dried glassware under an inert nitrogen atmosphere unless otherwise stated. When the reactions involved extraction with dichloromethane ($CH_2Cl_2$), chloroform ($CHCl_3$), ethyl acetate (EtOAc), or ethyl ether ($Et_2O$), the organic solutions were dried with anhydrous $Na_2SO_4$ and concentrated with a rotary evaporator under reduced pressure. Flash column chromatography was conducted using silica gel 60a, "40 Micron Flash" [32-63 μm] (Scientific Adsorbents, Inc.). Melting points were determined using the MEL-TEMP 3.0 apparatus and left uncorrected. $^1$H NMR spectra were recorded at 300 MHz on a Varian Mercury-VX spectrometer with $CDCl_3$ as solvent and tetramethylsilane (TMS) as the internal standard. All chemical shift values are reported in ppm ( ) Elemental analyses (C, H, N) were determined by Atlantic Microlab, Inc.

EXAMPLE 1

This example demonstrates reactions yielding fluoroalkoxy 2-hydroxybenzamide analogs. As illustrated in FIG. 1, Scheme I involves condensation of compounds 1a and 1b with a substituted salicylic acid to give the corresponding substituted 2-hydroxybenzamide analogs, 2a-e. Alkylation of the ortho hydroxyl group with 2-bromo-1-fluoroethane using potassium carbonate as a base produced 3a-e in moderate to high yield. Compound 3f was prepared by iodination of the corresponding tin precursor, 3g, which was prepared from 3b using standard stannylation reaction conditions. Compounds, 3a-f, were then converted into either the hydrochloride or oxalic acid salts for the in vitro $\sigma_1$ and $\sigma_2$ receptor binding assays.

EXAMPLE 2

Figure 2:
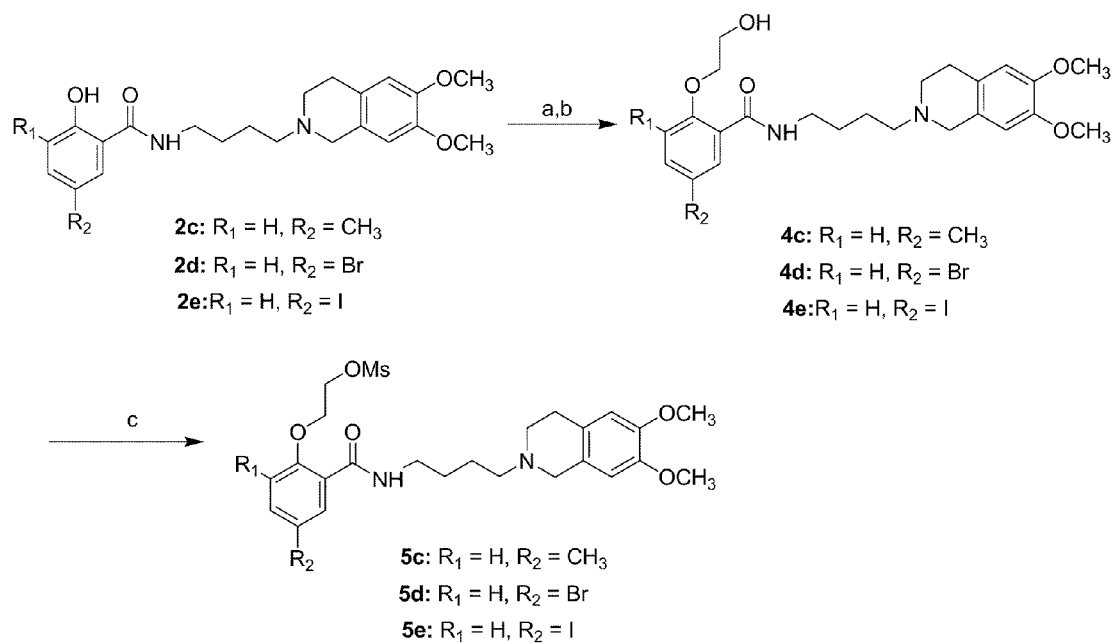
FIG. 2 illustrates scheme II for synthesis of some compounds of the present teachings.
Figure 3:
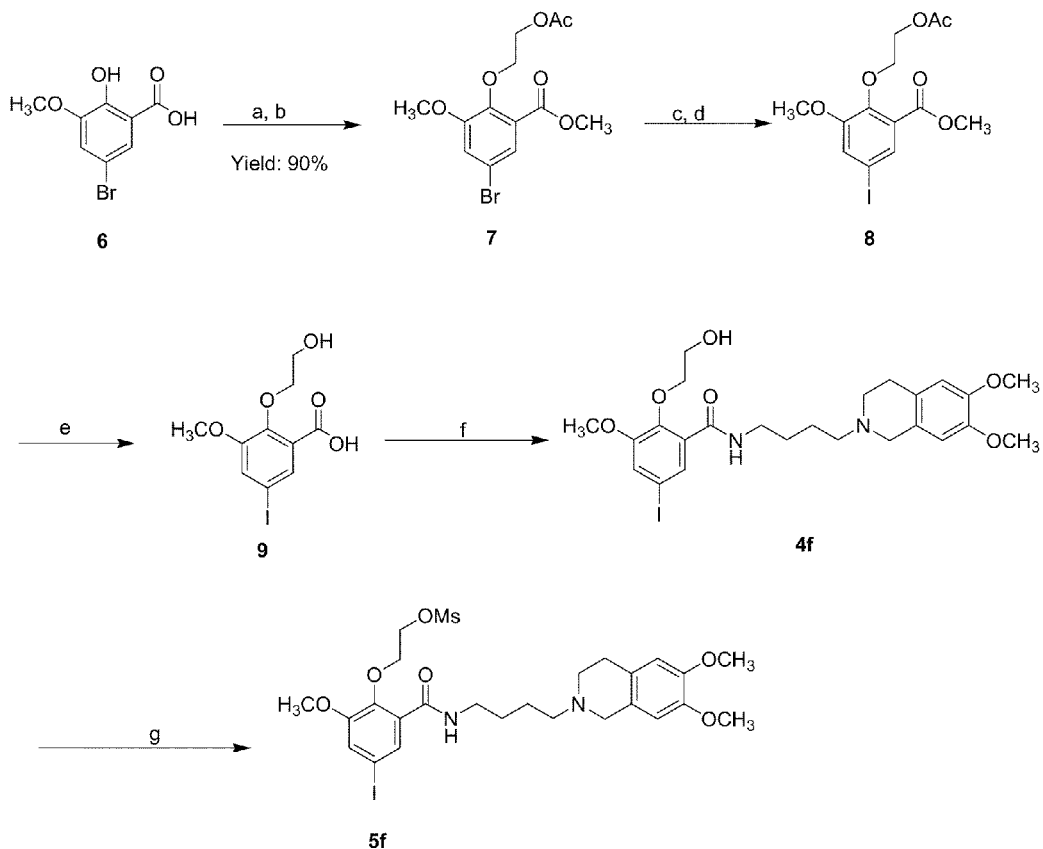
FIG. 3 illustrates scheme III for synthesis of some compounds of the present teachings.
Figure 4:
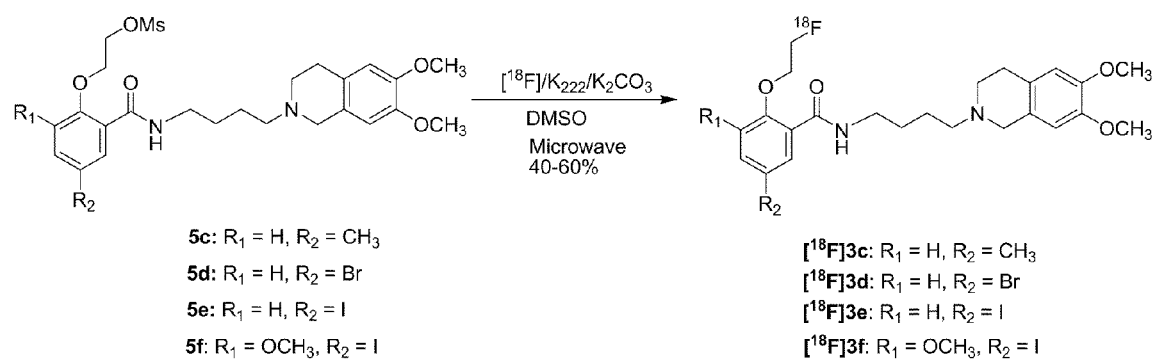
FIG. 4 illustrates scheme IV for synthesis of some compounds of the present teachings.

This example illustrates synthetic steps for generating $^{18}$F-tagged compounds of the present teachings. In this example, compounds 3c-f were radiolabeled with $^{18}$F as shown in Schemes II-IV (FIGS. 2, 3 and 4, respectively). Scheme II (FIG. 2) outlines the synthesis of the mesylate precursors required for the radiolabeling procedure. Alkylation of the ortho hydroxyl group of compounds, 2c-e, with 1-bromoethyl acetate followed by hydrolysis of the acetate group produced the corresponding 2-hydroxyethyl analogs, 4c-e, in good yield. Compounds, 4c-e, were then converted to the corresponding mesylates, 5c-e, by treatment with methanesulfonyl chloride in dichloromethane using triethylamine as an acid scavenger.

EXAMPLE 3

This example illustrates synthesis of the precursor for the corresponding 5-iodo analog, 5f, as shown in Scheme III (FIG. 3). Esterification of 5-bromo-2-methoxy salicylic acid followed by alkylation of the ortho hydroxyl group with 1-bromoethyl acetate, then hydrolysis of the acetate and benzoate esters produced the corresponding 2-hydroxyethyl analog, 9. Condensation of 9 with the amine, 1b, gave the amide, 4f, which was converted to the corresponding mesylate, 5f, using the conditions described above for the analogs, 5c-e.

EXAMPLE 4

This example illustrates synthesis of [$^{18}$F]3c, [$^{18}$F]3d, [$^{18}$F]3e, and [$^{18}$F]3f from mesylate precursors. As shown in Scheme IV (FIG. 4), mesylate precursors, compounds 5c-f, were treated with [$^{18}$F]fluoride/potassium carbonate and 4,7,13,16,21,24-Hexaoxa-1,10-diazabicyclo[8.8.8]-hexacosane (Kryptofix 222®, Acros Organics N.V., Fairlawn, N.J.) using dimethyl sulfoxide (DMSO) as the solvent. The reaction mixture was irradiated for 30-40 seconds in a microwave oven, and the crude product separated from the unreacted [$^{18}$F] fluoride using a C-18 reverse phase Sep-Pak® cartridge (Waters Corp., Milford, Mass.) and methanol as the eluant. The crude product was then purified by high-performance liquid chromatography (HPLC) using a C-18 reverse phase column. The entire procedure required ~2 h, and the radiochemical yield, corrected for decay to the start of synthesis, was 20~30%. The specific activities ranged from 1500-2500 Ci/mmol.

EXAMPLE 5

This example illustrates in vitro binding studies with the compounds of the present teachings. In this example, in vitro binding studies were conducted in order to measure the affinity of the target compounds for $\sigma_1$ and $\sigma_2$ receptors.

In these assays, the novel sigma ligands were dissolved in N,N-dimethylformamide (DMF), DMSO or ethanol, and then diluted in 50 mM Tris-HCl buffer containing 150 mM NaCl and 100 mM EDTA at pH 7.4 prior to performing the $\sigma_1$ and $\sigma_2$ receptor binding assays The procedures for isolating the membrane homogenates and performing the $\sigma_1$ and $\sigma_2$ receptor binding assays have been described in detail previously (Xu, J., et al., Eur. J. Pharmacol. 21: 525 (1-3): 8-17, 2005. Briefly, the $\sigma_1$ receptor binding assays were conducted in 96-well plates using guinea pig brain membrane homogenates (~300 μg protein) and ~5 nM [$^3$H](+)-pentazocine (34.9 Ci/mmol, Perkin Elmer, Boston, Mass.). The total incubation time was 90 min at room temperature. Nonspecific binding was determined from samples that contained 10 μM of cold haloperidol. After 90 min, the reaction was terminated by the addition of 150 μL of ice-cold wash buffer (10 mM Tris-HCl, 150 mM NaCl, pH 7.4) using a 96 channel transfer pipette (Fisher Scientific, Pittsburgh, Pa.). The samples were harvested and filtered rapidly through a 96-well fiber glass filter plate (Millipore, Billerica, Mass.) that had been presoaked with 100 μL of 50 mM Tris-HCl buffer at pH 8.0 for 1 h. Each filter was washed 3 times with 200 μL of ice-cold wash buffer, and the filter counted in a Wallac 1450 MicroBeta liquid scintillation counter (Perkin Elmer, Boston, Mass.).

The $\sigma_2$ receptor binding assays were conducted using rat liver membrane homogenates (~300 μg protein) and ~5 nM [$^3$H]DTG (58.1 Ci/mmol, Perkin Elmer, Boston, Mass.) in the presence of 1 μM (+)-pentazocine to block $\sigma_1$ sites. The incubation time was 120 min at room temperature. Nonspecific binding was determined from samples that contained 10 μM of cold haloperidol. All other procedures were identical to those described for the $\sigma_1$ receptor binding assay above.

Data from the competitive inhibition experiments were modeled using nonlinear regression analysis to determine the concentration that inhibits 50% of the specific binding of the radioligand (IC$_{50}$ value). Competitive curves were best fit to a one-site fit and gave pseudo-Hill coefficients of 0.6-1.0. $K_i$ values were calculated using the method of Cheng and Prusoff (Biochem. Pharmacol. 22: 3099-3108, 1973) and are presented as the mean±1 SEM. For these calculations, we used a $K_d$ value of 7.89 nM for [$^3$H](+)-pentazocine and guinea pig brain; for [$^3$H]DTG and rat liver, we used 30.73 nM[20]

The binding assays used [$^3$H](+)-pentazocine for the $\sigma_1$ receptors and [$^3$H]1,3-Di(2-tolyl)guanidine ([$^3$H]DTG) in the presence of 100 nM (+)-pentazocine for the $\sigma_2$ receptors. The $K_i$ values were determine from Scatchard plots. The results of the binding assays for compounds, 3a-f, are shown in Table I. Increasing the length of the spacer group from two carbons (3a) to 4 carbons (3c) results in a 69-fold increase in the affinity for $\sigma_1$ receptors, a 15-fold increase in the affinity for $\sigma_2$ receptors, and a 0.5 unit increase in the log D value; a measure of the lipophilicity of the compounds (Table I). Although four of the five compounds (3c-f) with a four-carbon spacer had higher affinities for $\sigma_1$ receptors (their $K_i$ values ranged from 330 to 2,150 nM) than the compound (3a) with a two-carbon spacer ($K_i$=22,750 nM), the affinities of 3c-f for $\sigma_2$ receptors increased proportionately more (their $K_i$ values ranged from 0.26 to 6.95 nM), leading to substantial increases in their ($\sigma_2$:$\sigma_1$) ratios (Table I).

The $\sigma_2$:$\sigma_1$ ratios for compounds, 3c-f, varied from 48 to 8,190. The excellent $\sigma_2$ receptor affinities and moderate to high $\sigma_2$:$\sigma_1$ ratios for the compounds, 3c-f, indicated that their corresponding $^{18}$F-labeled analogs would be useful radiotracers for imaging the $\sigma_2$ receptor status of solid tumors with PET. Also, the log D values for these compounds, a measure of their lipophilicity, are within the range that should lead to a high uptake in solid tumors (Xu, J., et al., Eur. J. Pharmacol. 21: 525 (1-3): 8-17, 2005).

TABLE I

Affinity ($K_i$) of the benzamide analogs, 6a-e, for the $\sigma_1$ and $\sigma_2$ receptors assayed in vitro

| | $K_i$ value (nM) | | | Log D[a] |
|---|---|---|---|---|
| | $\sigma_1$ | $\sigma_2$ | $\sigma_1$:$\sigma_2$ Ratio | (pH = 7.4) |
| 3a | 22,750 ± 3,410 | 102 ± 4 | 222 | 2.54 |
| 3b | 15,300 ± 2,305 | 386 ± 93 | 40 | 3.56 |
| 3c | 330 ± 25 | 6.95 ± 1.63 | 48 | 3.06 |
| 3d | 1,076 ± 88 | 0.65 ± 0.22 | 1,656 | 3.89 |
| 3e | 1,300 ± 225 | 1.06 ± 0.30 | 1,230 | 4.13 |
| 3f | 2,150 ± 410 | 0.26 ± 0.07 | 8,190 | 3.46 |

[a]calculated using the program ACD/log D

EXAMPLE 6

This example illustrates in vivo evaluation of compounds of the present teachings. All animal experiments were conducted in compliance with the Guidelines for the Care and Use of Research Animals established by Washington University's Animal Studies Committee. EMT-6 mouse mammary adenocarcinoma cells (5×10$^5$ cells in 100 uL of phosphate-buffered saline) were implanted subcutaneously in the scapular region of female Balb/c mice (~2-month old and 17-22 g; Charles River Laboratories). The biodistribution studies were initiated 7-10 days after implantation when the tumor size was ~0.2 cm$^3$ (~200 mg).

For the biodistribution studies, 10-120 μCi of [$^{18}$F]3c, [$^{18}$F]3d, [$^{18}$F]3e or [$^{18}$F]3f in 100-150 uL of saline was injected via the tail vein into EMT-6 tumor-bearing female Balb/c mice. Groups of at least 4 mice were used for each time point. At 5, 30, 60, and 120 min after injection, the mice were euthanized, and samples of blood, lung, liver, kidney, muscle, fat, heart, brain, bone and tumor were removed, weighed and counted in a Beckman Gamma 8000 well counter. After counting, the percentage of the injected dose per gram of tissue (% ID/g) was calculated. The tumor/organ ratios were calculated by dividing the % ID/g of the tumor by the % ID/g of each organ.

The results of the biodistribution studies in female Balb/c mice bearing EMT-6 tumors are shown in Table II. All four labeled compounds displayed excellent tumor uptake at 5 min post-injection, with values ranging from 2.5-3.7 percent of the injected dose per gram (% ID/g). Tumor uptake at 1 h post-injection remained high for each of the ligands, [$^{18}$F]3c, [$^{18}$F]3d, [$^{18}$F]3e and [$^{18}$F]3f, (1.14, 2.09, 2.72, and 2.15% ID/g, respectively), and continued to remain relatively high at 2 h post-injection (0.64, 0.96, 1.92 and 1.15% ID/g, respectively) compared to that of the normal tissues, fat and muscle. This resulted in acceptable tumor:normal tissue ratios for the PET imaging studies. For example, the tumor: muscle ratios ranged from 3-4 and the tumor:fat ratios ranged from 4.5-8 at 2 hrs post-injection, respectively. Also, the low bone uptake of all four labeled compounds, which continued to decrease between the 30 min and 1 h time points, suggests that these compounds do not undergo a significant defluorination in vivo.

Figure 6A:
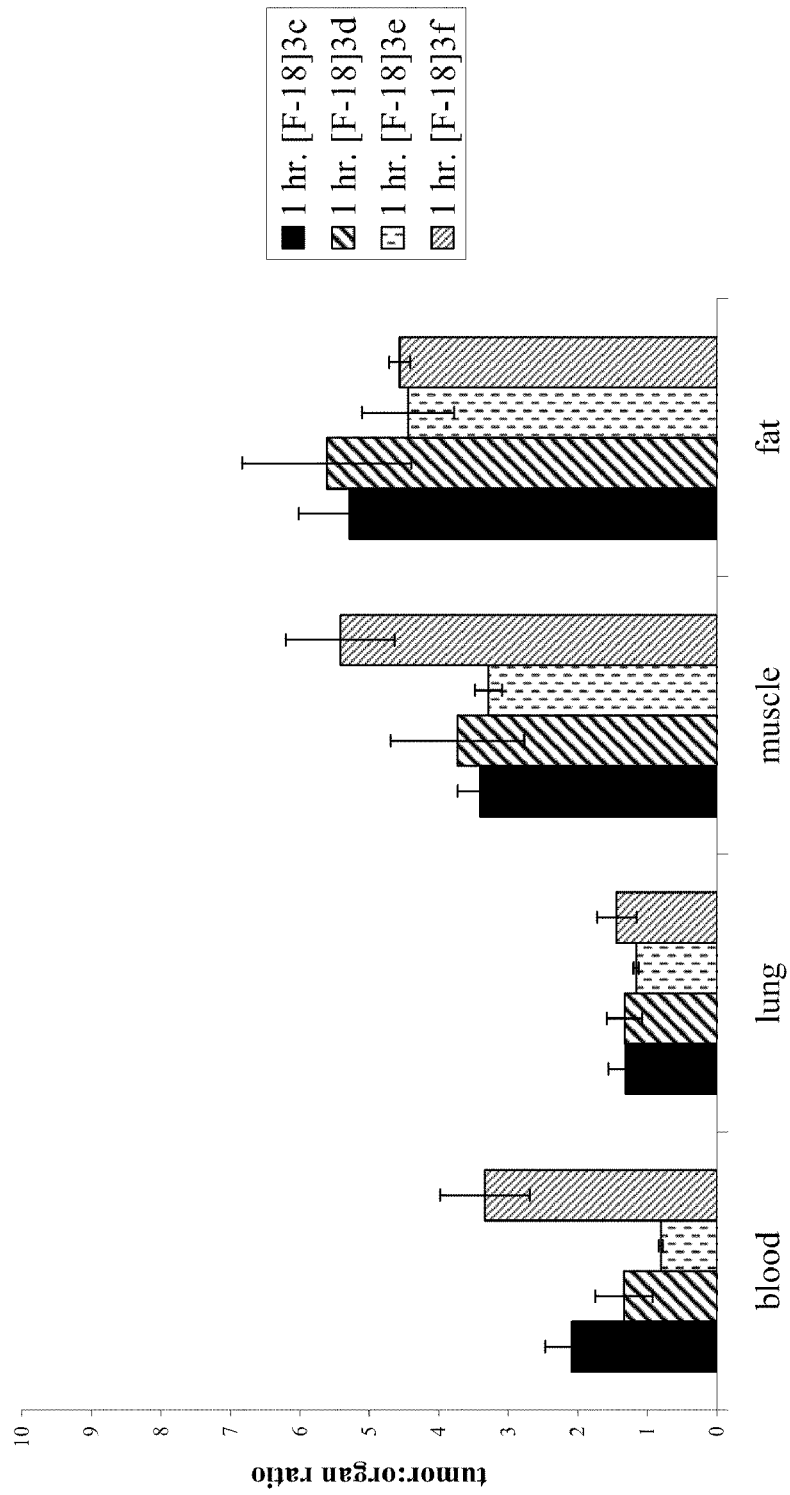
FIG. 6 illustrates tumor:organ ratios for the $^{18}$F-labeled $\sigma_2$ selective ligands, 3c-f, at 1 h (top) and 2 h (bottom) after i.v. injection into female Balb/c mice bearing EMT-6 tumors.
Figure 6B:
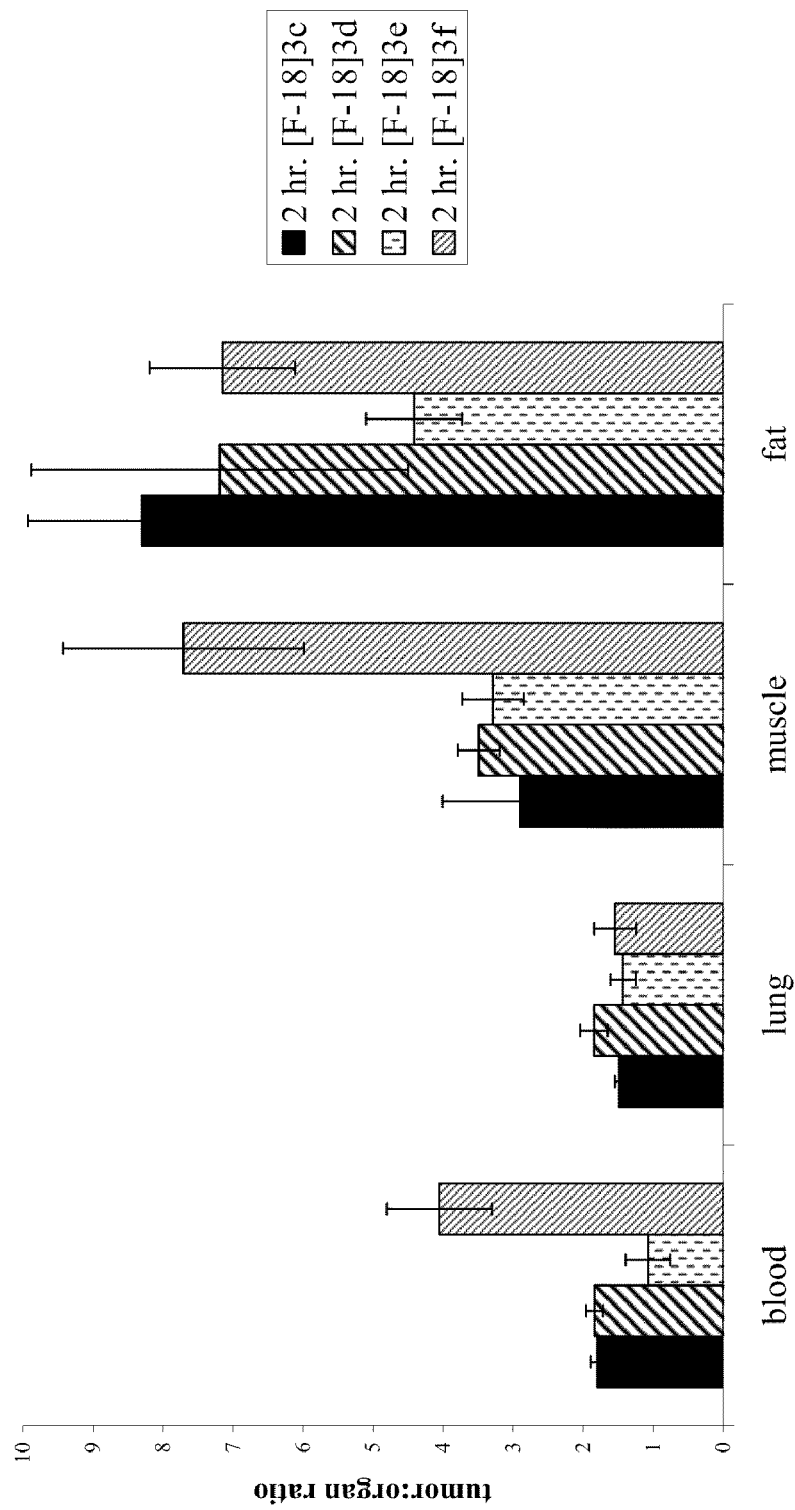

Compound [$^{18}$F]3f had the highest tumor:muscle ratio (~8) and a tumor:fat ratio of ~7 at 2 h after i.v. injection (FIG. 6A, B). The tumor:fat ratios for [$^{18}$F]3c and [$^{18}$F]3d were also high, reaching ~8 and ~6, respectively, at 2 h after i.v. injection. However, the tumor:muscle ratios for [$^{18}$F]3c and [$^{18}$F]3d were much lower than that for [$^{18}$F]3f. Although the tumor uptake of [$^{18}$F]3d and [$^{18}$F]3e is higher than that of [$^{18}$F]3c at both 1 h and 2 h post-injection, these radiotracers cleared much more slowly from the blood than [$^{18}$F]3c (Table II), making them less desirable than [$^{18}$F]3c as PET imaging agents. The moderate to high tumor:normal tissue ratios and the rapid clearance from the blood for [$^{18}$F]3c and [$^{18}$F]3f suggests that these radiotracers are likely the best candidates for imaging of solid tumors with PET. Consequently, these two radiotracers were selected for further studies to evaluate the suitability for detecting solid tumors and imaging their $\sigma_2$ receptor status with PET.

TABLE II

| | \[$^{18}$F\]3c-f Biodistribution in female Balb/c mice bearing EMT-6 tumors | | | | | | | |
|---|---|---|---|---|---|---|---|---|
| | 5 min. | 30 min. | 60 min. | 120 min. | 5 min. | 30 min. | 60 min. | 120 min. |
| | \[$^{18}$F\]3c | | | | \[$^{18}$F\]3d | | | |
| blood | 2.49 ± 0.49 | 1.16 ± 0.10 | 0.56 ± 0.08 | 0.35 ± 0.05 | 3.57 ± 0.43 | 2.81 ± 0.32 | 1.69 ± 0.63 | 0.52 ± 0.10 |
| lung | 10.26 ± 0.71 | 2.36 ± 0.19 | 0.88 ± 0.12 | 0.43 ± 0.07 | 12.08 ± 1.98 | 3.08 ± 0.23 | 1.60 ± 0.27 | 0.51 ± 0.08 |
| liver | 23.33 ± 4.22 | 10.51 ± 0.87 | 4.14 ± 0.55 | 2.05 ± 0.43 | 32.60 ± 3.96 | 13.12 ± 1.39 | 5.69 ± 0.54 | 2.30 ± 0.33 |
| kidney | 29.18 ± 1.92 | 6.86 ± 0.45 | 2.51 ± 0.51 | 0.87 ± 0.13 | 42.94 ± 3.34 | 17.55 ± 2.75 | 6.92 ± 1.61 | 1.12 ± 0.16 |
| muscle | 1.86 ± 0.08 | 0.70 ± 0.19 | 0.34 ± 0.05 | 0.24 ± 0.08 | 1.95 ± 0.19 | 0.98 ± 0.18 | 0.58 ± 0.11 | 0.28 ± 0.10 |
| fat | 1.95 ± 0.33 | 0.59 ± 0.13 | 0.22 ± 0.04 | 0.08 ± 0.02 | 2.85 ± 0.47 | 0.96 ± 0.13 | 0.38 ± 0.05 | 0.15 ± 0.06 |
| heart | 3.73 ± 0.15 | 1.15 ± 0.06 | 0.55 ± 0.07 | 0.27 ± 0.04 | 3.74 ± 0.37 | 1.55 ± 0.11 | 1.04 ± 0.21 | 0.40 ± 0.07 |
| brain | 0.76 ± 0.06 | 0.27 ± 0.05 | 0.18 ± 0.03 | 0.12 ± 0.02 | 1.09 ± 0.11 | 0.40 ± 0.03 | 0.32 ± 0.05 | 0.20 ± 0.03 |
| bone | 2.49 ± 0.19 | 0.96 ± 0.15 | 0.55 ± 0.07 | 0.45 ± 0.11 | 2.90 ± 0.39 | 1.17 ± 0.06 | 1.12 ± 0.16 | 1.28 ± 0.28 |
| tumor | 3.67 ± 0.45 | 2.54 ± 0.27 | 1.14 ± 0.10 | 0.64 ± 0.10 | 3.28 ± 0.41 | 2.59 ± 0.19 | 2.09 ± 0.28 | 0.96 ± 0.24 |
| | \[$^{18}$F\]3e | | | | \[$^{18}$F\]3f | | | |
| blood | 4.60 ± 0.44 | 4.30 ± 0.59 | 3.39 ± 0.29 | 1.92 ± 0.59 | 1.82 ± 0.25 | 1.23 ± 0.28 | 0.65 ± 0.09 | 0.28 ± 0.01 |
| lung | 9.71 ± 0.83 | 4.07 ± 0.46 | 2.34 ± 0.12 | 1.36 ± 0.24 | 18.47 ± 3.07 | 3.75 ± 0.58 | 1.51 ± 0.13 | 0.74 ± 0.03 |
| liver | 37.26 ± 4.88 | 17.35 ± 2.72 | 7.31 ± 0.98 | 4.25 ± 1.56 | 15.21 ± 2.21 | 10.73 ± 2.98 | 5.57 ± 0.31 | 2.61 ± 0.69 |
| kidney | 36.07 ± 2.28 | 17.43 ± 1.95 | 9.36 ± 0.90 | 3.92 ± 0.98 | 19.98 ± 1.66 | 7.73 ± 2.25 | 3.50 ± 0.80 | 1.34 ± 0.10 |
| muscle | 1.52 ± 0.10 | 1.12 ± 0.05 | 0.83 ± 0.04 | 0.60 ± 0.11 | 2.50 ± 0.33 | 0.73 ± 0.14 | 0.40 ± 0.07 | 0.15 ± 0.01 |
| fat | 2.32 ± 0.46 | 1.04 ± 0.06 | 0.62 ± 0.10 | 0.44 ± 0.08 | 4.13 ± 0.86 | 1.36 ± 0.50 | 0.47 ± 0.07 | 0.17 ± 0.05 |
| heart | 3.22 ± 0.27 | 2.37 ± 0.29 | 1.61 ± 0.11 | 1.00 ± 0.31 | 5.60 ± 0.45 | 1.54 ± 0.31 | 0.69 ± 0.06 | 0.39 ± 0.04 |
| brain | 0.55 ± 0.04 | 0.44 ± 0.04 | 0.36 ± 0.02 | 0.37 ± 0.06 | 0.71 ± 0.09 | 0.27 ± 0.04 | 0.14 ± 0.02 | 0.08 ± 0.01 |
| bone | 2.59 ± 0.28 | 1.31 ± 0.14 | 0.99 ± 0.07 | 1.67 ± 0.27 | 2.23 ± 0.56 | 2.01 ± 0.53 | 0.93 ± 0.16 | 0.59 ± 0.09 |
| tumor | 2.54 ± 0.62 | 2.81 ± 0.62 | 2.72 ± 0.13 | 1.92 ± 0.10 | 3.05 ± 0.43 | 3.11 ± 0.16 | 2.15 ± 0.25 | 1.15 ± 0.23 |

EXAMPLE 7

This example illustrates specificity of binding in vivo for $\sigma_2$ receptors by compounds of the present teachings.

Figure 7:
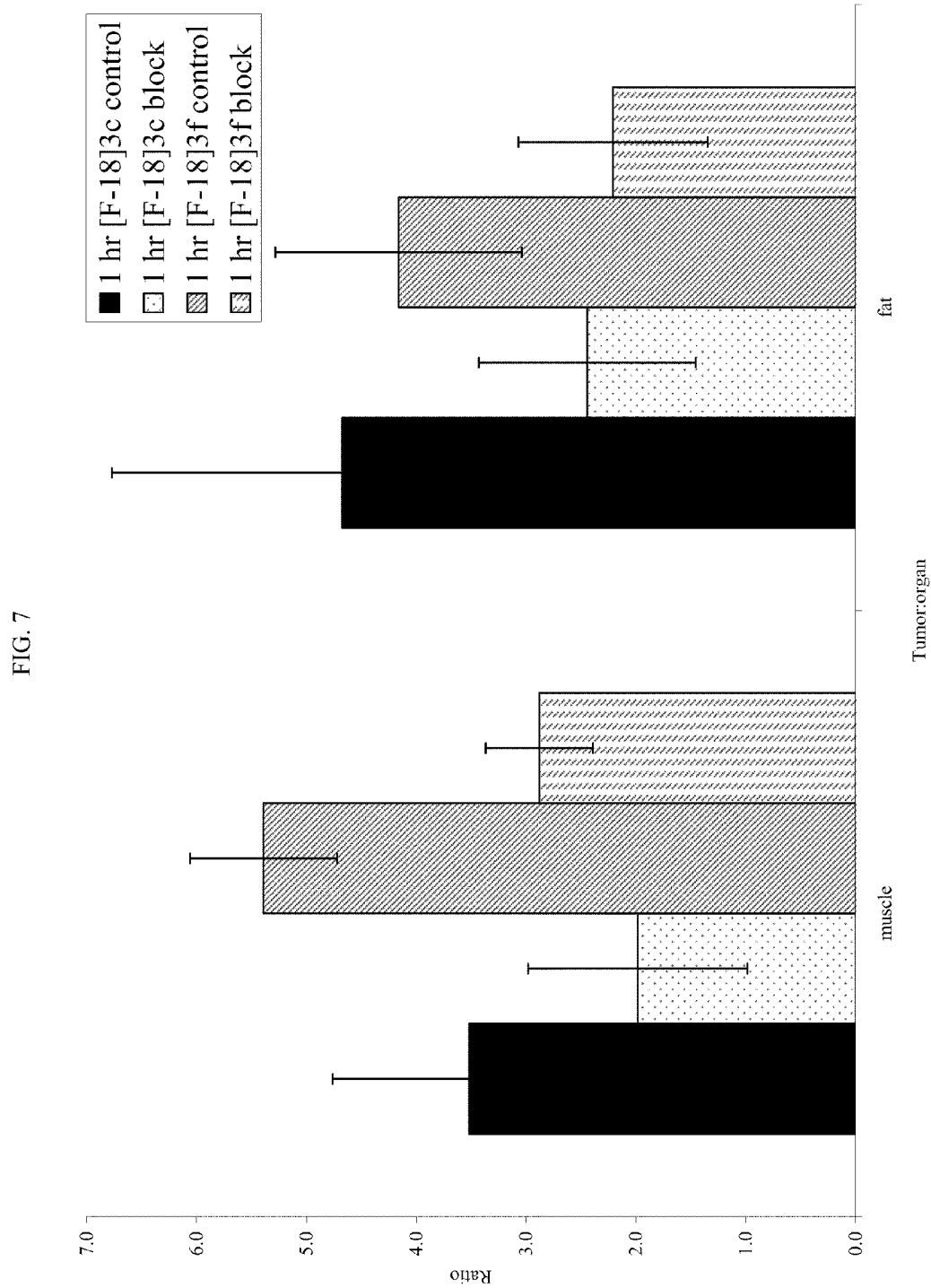
FIG. 7 presents a comparison of the tumor:fat and tumor:muscle ratios for [$^{18}$F]3c or [$^{18}$F]3f when there is no-carrier-added and when the $\sigma_1$ and $\sigma_2$ receptors are blocked with 1 mg/kg of YUN-143. All values were obtained 1 h after injection of the radiotracer.

In order to demonstrate that the in vivo binding of [$^{18}$F]3c and [$^{18}$F]3f is specific for $\sigma_2$ receptors, a no-carrier-added dose of these radiotracers was co-injected into EMT-6 tumor-bearing mice with N-(4-fluorobenzyl)piperidinyl-4-(3-bromophenyl)acetamide (YUN-143), a sigma ligand displaying a high affinity for both $\sigma_1$ and $\sigma_2$ receptors. Co-injection of YUN-143 with either [$^{18}$F]3c or [$^{18}$F]3f resulted in a significant decrease (~50%) in the tumor:muscle and tumor:fat ratios at 1 h post-injection (FIG. 7).

These blocking studies in tumor-bearing mice were conducted by co-injecting 1 mg/kg of cold N-(4-fluorobenzyl) piperidinyl-4-(3-bromophenyl)acetamide (YUN-143) with [$^{18}$F]3c or [$^{18}$F]3f. Yun-143 has a high affinity for both $\sigma_1$ and $\sigma_2$ receptors and is routinely used for sigma receptor blocking studies (Mach, R. H., et al., Nucl Med. Biol. 28: 451-458, 2001; Bowen, W. D. et al., Eur. J. Pharmacol. 278: 257-260, 1995; Bonhaus, D. W. et al., J. Pharmacol. Exp. Ther. 267: 961, 1993. All mice were sacrificed 60 min after injection of the radiotracer, and the tumor:organ ratios were determined as described above. The data presented in FIG. 7 indicate that both [$^{18}$F]3c and [$^{18}$F]3f bind selectively to $\sigma_2$ receptors in vivo.

EXAMPLE 8

This example illustrates use of radioligands of the present teachings as imaging agents.

To confirm the feasibility of using radioligands of the present teachings as PET imaging agents for determining the $\sigma_2$ receptor status of solid tumors, a CT/PET study using either [$^{18}$F]3c or [$^{18}$F]3f in female Balb/c mice bearing EMT-6 tumors was performed on a microPET-F220 (CTI-Concorde Microsystems Inc.) and a MicroCAT-II system (ImTek Inc.). For the microPET studies, each mouse was injected with ~0.25 mCi of either [$^{18}$F]3c or [$^{18}$F]3f via the tail vein and imaged 1 h later. MicroCT images were also obtained and co-registered with the PET images to determine the exact anatomical location of the radiotracers.

Figure 8:
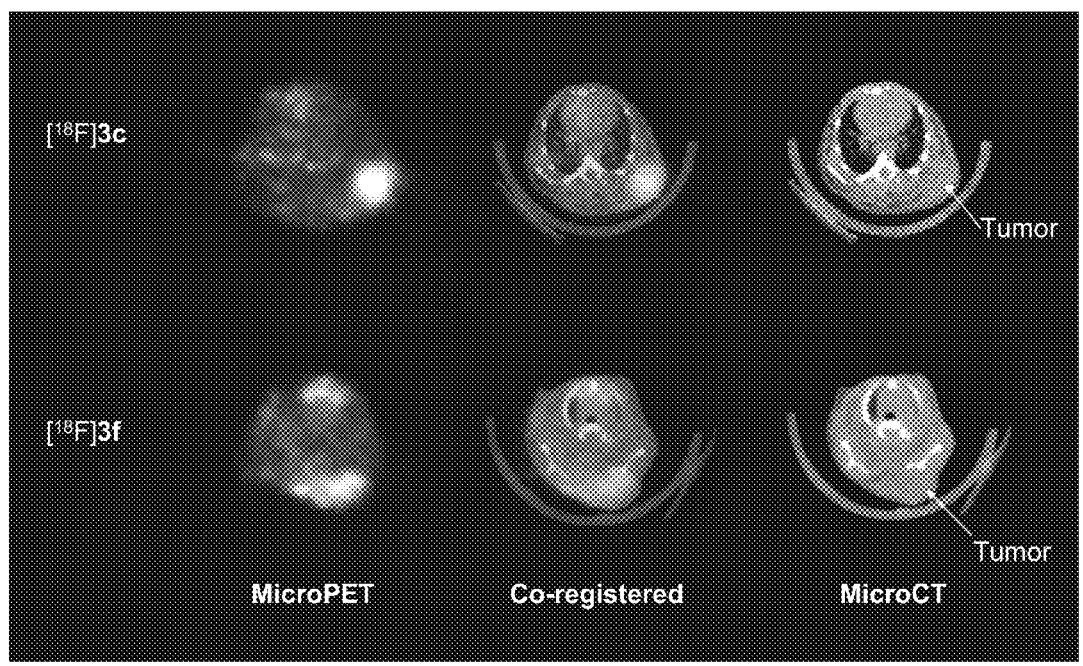
FIG. 8 illustrates microPET and microCT images of EMT-6 tumors in female Balb/c mice. All MicroPET images were acquired 1 h after i.v. injection of either [$^{18}$F] 3c or [$^{18}$F]3f.

In these studies, the EMT-6 tumors were readily identifiable using either radioligand, indicating that they are both acceptable agents for detecting solid tumors and imaging their $\sigma_2$ receptor status with PET (FIG. 8, EMT-6 Mouse Mammary Tumors).

EXAMPLE 9

This example describes a general method for synthesis of the substituted 2-hydroxybenzoic acid amides, compounds 2a-e, in particular compound 2a.

To synthesize N-[2-(6,7-dimethoxy-3,4-dihydro-1H-isoquinolin-2-yl)-ethyl]-2-hydroxy-5-methyl-benzamide (compound 2a), 1,3-dicyclohexycarbodimide (432.6 mg, 2.1 mmol) and 1-hydroxybenzotriazole (283.8 mg, 2.10 mmol) were added to a ice-water bath cooled solution of 1a (472.0 mg, 2.0 mmol) and 2-hydroxy-5-methyl-benzoic acid (152 mg, 2.0 mmol) in 30 ml dichloromethane. After the reaction mixture was stirred overnight, analysis of the products using thin layer chromatography with 20% methanol and 80% ethyl ether as the mobile phase indicated that the reaction was complete. After completion of the reaction, another 50 ml of dichloromethane was added to the mixture. The organic solution was then washed with an aqueous saturated NaHCO$_3$ solution and brine, sequentially. The organic solution was dried with anhydrous sodium sulfate. After removal of the solvent, the crude product was purified by column chromatography using 20% methanol and 80% ethyl ether as the mobile phase. The yield of 2a was 37.1%. The $^1$H-NMR spectrum (300 MHz, CDCl$_3$) of the purified product was: 2.25 (s, 3H), 2.75-2.95 (m, 6H), 3.58-3.65 (m, 4H), 3.82-3.83 (s, 6H), 6.48-6.51 (s, 1H), 6.62-6.63 (s, 1H), 6.82-6.85 (d, 1H), 7.02 (s, 1H), 7.08 (s, 1H), 7.20 (d, 1H). LCMS m/e: 371.2 (M+H).

EXAMPLE 10

This example illustrates synthesis of 5-Bromo-N-[4-(6,7-dimethoxy-3,4-dihydro-1H-isoquinolin-2-yl)-butyl]-2-hydroxy-3-methoxy-benzamide (compound 2b).

Compound 2b was prepared from 5-bromo-2-hydroxy-3-methoxy-benzoic acid and 1b as described above for 2a. The yield of 2b was 16.7%. The $^1$H-NMR spectrum (300 MHz, CDCl$_3$) of the purified product was: 1.73-1.76 (m, 4H), 2.57-2.59 (m, 2H), 2.76-2.81 (m, 4H), 3.45-3.47 (m, 2H), 3.58-3.61 (m, 2H), 3.82 (s, 3H), 3.86 (s, 3H), 3.88 (s, 3H), 6.48-6.51 (t, 1H), 6.56-6.59 (t, 1H), 6.97-7.00 (m, 1H), 7.07-7.10 (m, 1H). LCMS m/e: 493.10 (M+H).

EXAMPLE 11

This example illustrates synthesis of N-[4-(6,7-dimethoxy-3,4-dihydro-1H-isoquinolin-2-yl)-butyl]-2-hydroxy-5-methyl-benzamide (compound 2c).

Compound 2c was prepared from 2-hydroxy-5-methyl-benzoic acid and 1b as described above for 2a. The yield of 2c was 45%. The $^1$H-NMR spectrum (300 MHz, CDCl$_3$) of the purified product was: 1.75 (m, 4H), 2.12 (s, 3H), 2.58 (m, 2H), 2.75-2.77 (m, 2H), 2.82-2.84 (m, 2H), 3.40-3.50 (m, 2H), 3.58 (s, 2H), 3.83 (s, 3H), 3.85 (s, 3H), 6.50 (s, 1H), 6.60 (s, 1H), 6.85-6.88 (d, 1H), 7.06 (s, 1H), 7.13-7.16 (d, 2H), 7.61 (s, 1H). LCMS m/e: 399.20 (M+H).

EXAMPLE 12

This example illustrates synthesis of N-[4-(6,7-dimethoxy-3,4-dihydro-1H-isoquinolin-2-yl)-butyl]-2-hydroxy-5-bromo-benzamide (compound 2d).

Compound 2d was prepared form 5-bromo-2-hydroxybenzoic acid and 1b as described above for 2a. The yield of 2d was 28.0%. The $^1$H-NMR spectrum (300 MHz, CDCl$_3$) of the purified product was: 1.71-1.81 (m, 4H), 2.55-2.85 (m, 6H), 3.44-3.48 (m, 2H), 3.58-3.60 (m, 2H), 3.82 (s, 3H), 3.89 (s, 3H), 6.50 (s, 1H), 6.59 (s, 1H), 6.82-6.84 (d, 1H), 7.30-7.40 (d, 1H), 7.52 (d, 1H), 8.30 (s, 1H). Anal. (C$_{22}$H$_{27}$BrN$_2$O$_4$.1.25H$_2$O) C, H, N.

EXAMPLE 13

This example illustrates synthesis of N-[4-(6,7-dimethoxy-3,4-dihydro-1H-isoquinolin-2-yl)-butyl]-2-hydroxy-5-iodo-benzamide (2e).

Compound 2e was prepared form 2-hydroxy-5-iodo-benzoic acid and 1b as described above for 2a. The yield of 2e was 27.0%. The $^1$H-NMR spectrum (300 MHz, CDCl$_3$) of the purified product was: 1.69-1.81 (m, 4H), 2.54-2.65 (m, 2H), 2.75-2.83 (m, 2H), 3.44-3.48 (m, 2H), 3.58 (s, 2H), 3.82 (s, 3H), 3.85 (s,3H), 6.50 (s, 1H), 6.58 (s, 1H), 6.70-6.74 (d, 1H), 7.54-7.55 (d, 1H), 7.65-7.67 (d, 1H), 8.20 (s, 1H). Anal. (C$_{22}$H$_{27}$IN$_2$O$_4$.0.75H$_2$O) C, H, N.

EXAMPLE 14

This example describes a general method for synthesis of the substituted 2-(2-fluoroethoxy)benzoic acid amides, 3a-e, in particular compound 3a.

To synthesize [N-(6,7-dimethoxy-3,4-dihydro-1H-isoquinolin-2-yl)-ethyl]-2-(2-fluoro-ethoxy)-5-methyl-benzamide (compound 3a), potassium carbonate (792.5 mg, 4.88 mmol) was added to a solution of 2a (278 mg, 0.75 mmol) and 2-bromo-1-fluoroethane (620 mg, 4.88 mmol) in acetone (60 mL). The reaction mixture was refluxed for 48 h until the reaction was complete as determined by thin layer chromatography with 5% methanol and 95% ethyl ether as the mobile phase. The solvent was evaporated, 30 ml of water added to the flask, and then the mixture extracted with dichloromethane (25 mL×3). After the organic layer was dried with anhydrous sodium sulfate, the crude product was purified by column chromatography using 5% methanol and 95% ethyl ether as the mobile phase. The yield of 3a was 90%. The $^1$H-NMR spectrum (300 MHz, CDCl$_3$) of the purified product was: 2.33 (s, 3H), 2.64-2.80 (m, 6H), 3.63-3.75 (m, 4H), 3.84 (s, 3H), 3.86 (s, 3H), 4.16 (m, 1H), 4.21 (m, 1H), 4.41 (m, 1H), 4.60 (m, 1H), 6.55 (s, 1H), 6.61 (s, 1H), 6.78-6.81 (d, 1H), 7.20 (d, 1H), 8.00 (s, 1H), 8.28 (s, 1H). LCMS m/e: 417.22 (M+H). For the in vitro binding experiments, the free base was converted into the hydrochloride salt; m.p. 159-161° C., Anal. (C$_{23}$H$_{30}$ClFN$_2$O$_4$). C. H. N.

EXAMPLE 15

This example illustrates synthesis of 5-bromo-N-[4-(6,7-dimethoxy-3,4-dihydro-1H-isoquinolin-2-yl)-butyl]-2-(2-fluoro-ethoxy)-3-methoxy-benzamide (compound 3b).

Compound 3b was prepared from 2b as described for 3a above. The yield was 50%. The $^1$H-NMR spectrum (300 MHz, CDCl$_3$) of the purified product was: 1.64 (m, 4H), 2.48-2.52 (t, 3H), 2.64-2.66 (t, 3H), 2.74-2.78 (t, 3H), 3.42-3.55 (m, 4H), 3.79-3.87 (m, 9H), 4.19-4.22 (t, 2H), 4.29-4.32 (t, 2H), 4.58-4.61 (t, 2H), 4.74-4.77 (t, 2H), 6.47 (s, 1H), 6.54 (s, 1H), 7.07 (d, 1H), 7.78 (d, 1H), 8.10 (s, 1H). For the in vitro binding experiments, the free base was converted into the oxalic acid salt; m.p. 127-129° C. LCMS m/e: 590.30 (M+Li). Anal. (C$_{26}$H$_{33}$BrFN$_2$O$_7$).

EXAMPLE 16

This example illustrates synthesis of N-[6,7-dimethoxy-3,4-dihydro-1H-isoquinolin-2-yl-butyl]-2-(2-fluoro-ethoxy)-5-methyl-benzamide (compound 3c).

Compound 3c was prepared from 2c as described above for 3a. The yield of 3c was 67%. The $^1$H-NMR spectrum (300 MHz, CDCl$_3$) of the purified product was: 1.67-2.00 (m, 4H), 2.33 (s, 3H), 2.51-2.56 (t, 3H), 2.67-2.72 (t, 3H), 3H), 2.78-2.82 (t, 3H), 3.48-3.54 (m, 4H), 3.82 (s, 3H), 3.83 (s, 3H), 4.21-4.24 (t, 1H), 4.30-4.33 (t, 1H), 4.68-4.71 (t, 1H), 4.84-4.87 (t, 1H), 6.49 (s, 1H), 6.57 (s, 1H), 6.79-6.82 (d, 1H), 7.20 (m, 1H), 7.96 (s, 1H), 7.99-7.80 (d, 1H). LCMS m/e: 445.25 (M+H). For the in vitro binding experiments, the free base was converted into the oxalic acid salt; m.p. 131-133° C. Anal. (C$_{26}$H$_{34}$FN$_2$O$_6$).

EXAMPLE 17

This example illustrates synthesis of N-[4-(6,7-dimethoxy-3,4-dihydro-1H-isoquinolin-2-yl)-butyl]-2-(2-fluoro-ethoxy)-5-bromo-benzamide (compound 3d).

Compound 3d was prepared from 2d as described above for 3a. The yield of 3d was 38.90%. The $^1$H-NMR spectrum (300 MHz, CDCl$_3$) of the purified product was: 1.57-1.80 (m, 4H), 2.62-2.66 (m, 3H), 2.78-2.82 (m, 3H), 3.48-3.51 (m, 2H), 3.60-3.64 (m, 2H), 3.82 (s, 3H), 3.83 (s, 3H), 4.21-4.25 (t, 1H), 4.31-4.35 (t, 1H), 4.70-4.74 (t, 1H), 4.86-4.90 (t, 1H), 6.49 (s, 1H), 6.57 (s, 1H), 6.78-6.82 (d, 1H), 7.48-7.52 (d, 1H), 7.96 (s, 1H), 8.26 (d, 1H). LCMS m/e: 509.1 (M+H). For the in vitro binding experiments, the free base was converted into the oxalic acid salt; m.p. 119-121° C. Anal. (C$_{25}$H$_{31}$BrFN$_2$O$_6$).

EXAMPLE 18

This example illustrates synthesis of N-[4-(6,7-dimethoxy-3,4-dihydro-1H-isoquinolin-2-yl)-butyl]-2-(2-fluoro-ethoxy)-5-iodo-benzamide (compound 3e).

Compound 3e was prepared from 2e as described above for 3a. The yield of 3e was 41.4%. The $^1$H-NMR spectrum (300 MHz, CDCl$_3$) of the purified product was: 1.61-1.72 (m, 4H), 2.46-2.52 (m, 2H), 2.67-2.71 (m, 2H), 2.76-2.78 (m, 2H), 3.41-3.47 (m, 2H), 3.52 (t, 2H), 3.80 (s, 3H), 3.83 (s, 3H), 4.19-4.21 (m, 1H), 4.27-4.31 (m, 1H), 4.67-4.71 (m, 1H), 4.83-4.86 (m, 1H), 6.46 (s, 1H), 6.55 (s, 1H), 6.62-6.66 (d, 1H), 7.62-7.67 (m, 1H), 7.87 (s, 1H), 8.40-8.41 (d, 1H). LCMS m/e: 557.13 (M+H). For the in vitro binding experiments, the free base was converted into the oxalic acid salt; m.p. 121-123° C. Anal. (C$_{25}$H$_{31}$FIN$_2$O$_6$).

EXAMPLE 19

This example describes a general method for synthesis of the substituted 5-bromo-benzoic acid derivatives into their substituted 5-tributylstannanyl benzoic acid derivatives. in particular compound 3g.

To synthesize N-[4-(6,7-dimethoxy-3,4-dihydro-1H-isoquinolin-2-yl)-butyl]-2-(2-fluoro-ethoxy)-3-methoxy-5-tributylstannanyl-benzamide (compound 3g), Nitrogen was bubbled for 5-10 min through a solution of 3b (200 mg, 0.371 mmol) in 20 ml fresh distilled toluene. The whole system was covered with aluminum foil. Tetrakis(triphenylphosphine palladium(0) [(PPh$_3$)$_4$Pd(0)] (42 mg, 0.036 mmol) and bis(tributylin) [Sn(C$_4$H$_9$)$_3$]$_2$ (575 mg, 0.99 mmol) was added to the reaction mixture and heated overnight at 110° C. with an oil bath. Thin layer chromatography with 45% hexane, 45% ethyl ether and 10% methanol as the mobile phase was used to assess when the reaction was complete. After quenching the reaction, the crude product was purified on a silica gel column to isolate the tin intermediate, 3g. The yield of 3g was 64%. The $^1$H-NMR spectrum (300 MHz, CDCl$_3$) of the purified product was: 0.87-1.58 (m, 27H), 1.61-1.69 (m, 4H), 2.56 (s, 2H), 2.72 (s, 2H), 2.81-2.82 (s, 2H), 3.47-3.49 (d, 2H), 3.57 (s, 2H), 3.83 (s, 6H), 3.88 (s, 3H), 4.25 (d, 1H), 4.37 (s, 1H), 4.62-4.65 (s, 1H), 4.78-4.81 (s, 1H), 6.51 (s, 1H), 6.58 (s, 1H), 7.81 (s, 1H), 8.07 (s, 1H). LCMS m/e: 747.60 (M–H).

EXAMPLE 20

This example illustrates a general method for converting the tin precursor of the benzoic acid derivatives into their corresponding iodine substituted benzoic acid derivatives, in particular compound 3f.

To synthesize (N-[4-(6,7-Dimethoxy-3,4-dihydro-1H-isoquinolin-2-yl)-butyl]-2-(2-fluoro-ethoxy)-3-methoxy-5-iodo-benzamide (3f), a solution of iodine in CHCl$_3$ (5 mL, 0.5 M) was added dropwise to a solution of the tin precursor, 3g (258 mg, 0.34 mmol) in 20 ml CH$_2$Cl$_2$ until the color of the solution persisted. The reaction was stirred at room temperature for 30 min, and a solution of 5% aqueous NaHSO$_3$ was added until the solution was colorless. The mixture was extracted with CH$_2$Cl$_2$, and the organic layers washed with brine before being dried with Na$_2$SO$_4$. The organic layers were then concentrated under vacuum and purified using a silica gel column with 15% methanol and 85% ether as the mobile phase to isolate 3f. The yield of 3f was 36%. The $^1$H-NMR spectrum (300 MHz, CDCl$_3$) of the purified product was: 1.60-1.80 (m, 2H), 1.80-2.10 (m, 4H), 3.19-3.2 (m, 2H), 3.40-3.50 (m, 2H), 3.68 (m, 2H), 3.83 (m, 2H), 3.92 (s, 3H), 3.95 (s, 3H), 3.99 (s, 3H), 4.26 (t, 1H), 4.37 (s, 1H), 4.65 (s, 1H), 4.80 (s, 1H), 6.50 (s, 1H), 6.58 (s, 1H), 7.28 (d, 1H), 8.02 (d, 1H), 8.21 (s, 1H). LCMS m/e: 587.14 (M+H). For the in vitro binding experiments, the free base was converted into the oxalic acid salt; m.p. 125-127° C. Anal. (C$_{26}$H$_{33}$FIN$_2$O$_7$).

EXAMPLE 21

This example describes a general method for converting the substituted 2-hydroxy benzoic acid derivatives into their substituted 2-(2-hydroxy-ethoxy)-benzoic acid amides, in particular compound 4c.

To synthesize N-[4-6,7-dimethoxy-3,4-dihydro-1H-isoquinolin-2-yl)-butyl]-2-(2-hydroxy-ethoxy)-5-methyl-benzamide (compound 4c), anhydrous potassium carbonate (546.0 mg, 3.26 mmol) was added to a solution of 2c (200.0 mg, 0.5 mmol) and 2-bromoethyl acetate (547.0 mg, 3.27 mmol) in 60 mL of acetone. The reaction mixture was refluxed for 48 h under nitrogen. After 48 h, thin layer chromatography with 15% methanol and 85% ether as the mobile phase indicated that the reaction was complete. After evaporating the solvent, the residue was dissolved in 30 ml of water and extracted with ethyl acetate (20×3 mL). Then the organic component was washed with brine, dried with anhydrous sodium sulfate, concentrated, and the final product purified on a silica gel column to isolate the 2-{2-[4-(6,7-dimethoxy-3,4-dihydro-1H-isoquinolin-2-yl)-butylcarbamoyl]-4-methyl-phenoxy}-ethyl ester. The yield of this intermediate was 82.2%. The $^1$H-NMR spectrum (300 MHz, CDCl$_3$) of the purified product was: 1.70 (m, 4H), 2.01 (s, 3H), 2.33 (s, 3H), 2.56 (m, 2H), 2.71-2.73 (m, 2H), 2.81 (m, 2H), 3.50-3.52 (m, 2H), 3.55 (s, 2H), 3.83 (s, 3H), 3.84 (s, 3H), 4.23 (t, 2H), 4.50 (t, 2H), 6.50 (s, 1H), 6.58 (s, 1H), 6.78-6.82 (d, 1H), 7.18-7.25 (d, 1H), 7.95 (s, 1H), 8.02 (s, 1H).

NaOH (30 mg, 0.75 mmol) was added to a solution of this intermediate (182 mg, 0.375 mmol) in 20 mL of methanol and 10 mL of water. The reaction mixture was stirred overnight until the reaction was complete. Then 0.375 mL of 2 N HCl was added to neutralize the solution. After evaporating the solvent, the residue was dissolved in 60 mL of ethyl acetate. The solution was washed first with water, then brine, and finally dried with anhydrous sodium sulfate. After evaporating the solvent, the crude product was purified on a silica gel column. The yield of 4c was 96%. The $^1$H-NMR spectrum (300 MHz, CDCl$_3$) of the purified product was: 1.68-1.85 (m, 4H), 2.39 (s, 3H), 2.45 (s, 1H), 2.51-2.61 (m, 2H), 2.80-2.87 (m, 4H), 3.45-3.61 (m, 4H), 3.76-3.80 (t, 2H), 3.83 (s, 3H), 3.85 (s, 3H), 3.83 (s, 3H), 4.05-4.08 (t, 2H), 6.49 (s, 1H), 6.60 (s, 1H), 6.79-6.83 (d, 1H), 7.15-7.19 (d, 2H), 7.93 (s, 1H), 8.30 (s, 1H).

EXAMPLE 22

This example illustrates synthesis of 5-Bromo-N-[4-(6,7-dimethoxy-3,4-dihydro-1H-isoquinolin-2-yl)-butyl]-2-(2-hydroxy-ethoxy)-benzamide (compound 4d).

Compound 4d was prepared from 2d as described above for 4c. The yield of compound 4d was 70%. The $^1$H-NMR spectrum (300 MHz, CDCl$_3$) of the purified product was: 1.65-1.90 (m, 4H), 2.66-2.70 (m, 2H), 2.92 (m, 4H), 3.51-3.54 (m, 2H), 3.72 (m, 2H), 3.72-3.81 (t, 2H), 3.83 (s, 3H), 3.85 (s, 3H), 4.05-4.09 (t, 2H), 6.51 (s, 1H), 6.60 (s, 1H), 6.77-6.81 (d, 1H), 7.44-7.48 (d, 2H), 8.17 (s, 1H), 8.30 (s, 1H).

EXAMPLE 23

This example illustrates synthesis of N-[4-(6,7-dimethoxy-3,4-dihydro-1H-isoquinolin-2-yl)-butyl]-2-(2-hydroxy-ethoxy)-5-iodo-benzamide (compound 4e).

Compound 4e was prepared from 2e as described above for 4c. The yield of 4e was 77%. The $^1$H-NMR spectrum (300 MHz, CDCl$_3$) of the purified product was: 1.60-1.90 (m, 4H), 2.63-2.66 (m, 3H), 2.90 (s, 2H), 3.52-3.55 (m, 2H), 3.70 (m, 2H), 3.79-3.82 (t, 2H), 3.83 (s, 3H), 3.85 (s, 3H), 4.08-4.10 (t, 2H), 6.50 (s, 1H), 6.60 (s, 1H), 6.67-6.70 (d, 1H), 7.60-7.70 (d, 1H), 8.30 (s, 1H), 8.40-8.41 (d, 1H).

EXAMPLE 24

This example describes a general method for converting the substituted 2-hydroxy-ethoxy benzoic acid amides of the present teachings to their methanesulfonic acid esters, in particular compound 5c.

To synthesize 2-(2-(4-(6,7-dimethoxy-3,4-dihydroisoquinolin-2(1H)-yl)butylcarbamoyl)-4-methylphenoxy)ethyl methanesulfonate (compound 5c), methanesulfonic chloride (120 mg, 1.04 mmol) was added to an ice-water cooled solution of 4c (354 mg, 0.8 mmol) and triethylamine (242 mg, 2.4 mmol) in 30 mL of dichloromethane. The reaction mixture was stirred for 3 h until thin layer chromatography using 5% methanol and 95% dichloromethane as the mobile phase indicated that the reaction was complete. After 3 h, 20 mL of dichloromethane was added, the solution was washed with first a saturated sodium carbonate aqueous solution (20 mL×3), then brine, and finally dried with anhydrous sodium sulfate. After evaporating the solvent, the crude product was purified on a silica gel column to isolate 5c. The yield of 5c was 81.6%. The $^1$H-NMR spectrum (300 MHz, CDCl$_3$) of the purified product was: 2.07-2.10 (m, 4H), 2.71 (s, 3H), 2.80-3.00 (m, 2H), 3.08-3.20 (m, 4H), 3.40 (m, 3H), 3.80-4.00 (m, 4H), 4.20 (s, 3H), 4.22 (s, 3H), 4.60-4.68 (t, 2H), 4.95-4.97 (t, 2H), 6.88 (s, 1H), 6.95 (s, 1H), 7.15-7.18 (d, 1H), 7.50-7.60 (d, 1H), 8.20 (s, 1H), 8.19 (s, 1H). Anal. (C$_{26}$H$_{36}$N$_2$O$_7$S) C, H, N.

EXAMPLE 25

This example illustrates synthesis of 2-(4-bromo-2-(4-(6,7-dimethoxy-3,4-dihydroisoquinolin-2(1H)-yl)butylcarbamoyl)phenoxy)ethyl methanesulfonate (compound 5d).

Compound 5d was prepared from 4d as described above for 5c. The yield of 5d was 77%. The $^1$H-NMR spectrum (300 MHz, CDCl$_3$) of the purified product was: 1.72-1.75 (m, 4H), 2.61-2.68 (m, 2H), 2.85 (s, 3H), 3.05 (s, 2H), 3.42-3.58 (m, 4H), 3.68 (s, 2H), 3.82 (s, 3H), 3.83 (s, 3H), 4.29 (t, 2H), 4.60 (t, 2H), 6.50 (s, 1H), 6.57 (s, 1H), 6.70-6.77 (d, 1H), 7.45-7.55 (d, 1H), 7.95 (s, 1H), 8.20-8.22 (d, 1H). LCMS m/e: 585.10 (M+H).

EXAMPLE 26

This example illustrates synthesis of 2-(2-(4-(6,7-dimethoxy-3,4-dihydroisoquinolin-2(1H)-yl)butylcarbamoyl)-4-iodophenoxy)ethyl methanesulfonate (compound 5e).

Compound 5e was prepared from 4e as described above for 5c. The yield of 5e was 80%. The $^1$H-NMR spectrum (300 MHz, CDCl$_3$) of the purified product was: 1.60-1.80 (m, 4H), 2.52-2.55 (m, 2H), 2.67-2.70 (m, 2H), 2.70-2.78 (m, 2H), 3.02 (s, 3H), 3.46-3.52 (m, 4H), 3.82 (s, 3H), 3.83 (s, 3H), 4.23-4.26 (t, 2H), 4.56-4.60 (t, 2H), 6.48 (s, 1H), 6.55 (s, 1H), 6.60-6.64 (d, 1H), 7.64-7.68 (d, 1H), 7.85 (s, 1H), 8.38-8.39 (d, 1H). LCMS m/e: 633.10 (M+H).

EXAMPLE 27

This example illustrates synthesis of 2-(2-Acetoxyethoxy)-5-bromo-3-methoxy-benzoic acid methyl ester (compound 7).

To prepare this compound, initially 1.0 mL of 98% concentrated sulfuric acid was added to a solution of 5-bromo-2-hydroxy-3-methoxy-benzoic acid, (compound 6) (1.0 g, 4.0 mmol) in 50 ml of methanol. The reaction mixture was refluxed overnight until thin layer chromatography using 20% ethyl acetate and 80% hexane as the mobile phase indicated that the reaction was complete. After evaporating the methanol, the residue was dissolved in 60 mL of ethyl acetate and washed with a saturated NaHCO$_3$ aqueous solution and then brine. After drying with anhydrous sodium sulfate, the solution was concentrated, and the crude product was purified on a silica gel column to isolate the intermediate, 5-bromo-2-hydroxy-3-methoxy-benzoic acid methyl ester. The yield of this intermediate was 94%. The $^1$H-NMR spectrum (300 MHz, CDCl$_3$) of the purified product was: 3.88 (s 3H), 3.95 (s, 3H), 7.09 (d, 1H), 7.55 (t, 1H), 10.96 (d, 1H).

Potassium carbonate (2.90 g, 21.0 mmol) was added to a solution of the above intermediate (0.84 g, 3.23 mmol) and 2-bromoethyl acetate (3.5 g, 20.96 mmol) in 60 mL of acetone. The reaction mixture was refluxed for 72 h until thin layer chromatography using 20% ethyl acetate and 80% hexane as the mobile phase indicated that the reaction was complete. After evaporating the solvent, the residue was dissolved in 30 mL of water and then extracted with ethyl acetate (25 mL×3). The organic solution was dried with anhydrous sodium sulfate, resuspended, and purified on a silica gel column. The yield of 7 was 78%. The $^1$H-NMR spectrum (300 MHz, CDCl$_3$) of the purified product was: 2.10 (s, 3H), 3.86 (s, 3H), 3.88 (s, 3H), 4.21-4.24 (t, 2H), 4.38-4.41 (t, 3H), 7.14 (s, 1H), 7.45 (s, 1H).

EXAMPLE 28

This example illustrates synthesis of 2-(2-Acetoxyethoxy)-5-iodo-3-methoxy-benzoic acid methyl ester (compound 8).

To synthesize compound 8, nitrogen was bubbled for 5-10 min through a solution of 2-(2-acetoxy-ethoxy)-5-bromo-3-methoxy-benzoic acid methyl ester, (compound 7) (270 mg, 0.778 mmol) in 20 mL of freshly distilled toluene. The reaction system was covered with aluminum foil. Tetrakis(triphenylphosphine) palladium(0) [(PPh$_3$)$_4$Pd(0)] (100 mg, 0.087 mmol) and bis(tributlytin) [Sn(C$_4$H$_9$)$_3$]$_2$ (899 mg, 1.55 mmol) were added to the reaction mixture and heated overnight at 110° C. in an oil-bath while stirring. After quenching, thin layer chromatography using 15% ethyl acetate and 85% hexane as the mobile phase indicated that the reaction was complete. The product was then purified on a silica gel column to isolate the tin precursor, 2-(2-acetoxy-ethoxy)-3-methoxy-5-tributylstannanyl-benzoic acid methyl ester. The yield of the tin precursor was 37.3%. The $^1$H-NMR spectrum (300 MHz, CDCl$_3$) of the purified product was: 0.8-1.75 (m, 27H), 2.10 (s, 3H), 3.87 (s, 3H), 3.89 (s, 3H), 4.24-4.27 (t, 2H), 4.38-4.41 (t, 2H), 7.09-7.30 (s 1H), 7.35 (s 1H).

A solution of iodine in CHCl$_3$ (5 mL, 0.5 M) was added dropwise to a solution of the above tin precursor (680 mg, 1.22 mmol) in 20 mL of CH$_2$Cl$_2$ until the color of the solution persisted. Then the reaction was stirred at room temperature for 30 min, and a quench solution of 5% aqueous NaHSO$_3$ was added until the solution became colorless. The mixture was extracted with CH$_2$Cl$_2$, and the organic layers washed with brine and dried by Na$_2$SO$_4$. The organic layers were then condensed under vacuum and purified using a silica gel column with 15% ethyl acetate and 85% hexane as the mobile phase. The yield of compound 8 was 90%. The $^1$H-NMR spectrum (300 MHz, CDCl$_3$) of the purified product was: 2.10

(s, 3H), 3.85 (s, 3H), 3.88 (s, 3H), 4.21-4.25 (t, 2H), 4.37-4.41 (t, 2H), 7.29-7.30 (s 1H), 7.63 (s 1H).

EXAMPLE 29

This example illustrates synthesis of 2-(2-Hydroxy-ethoxy)-5-iodo-3-methoxy-benzoic acid (compound 9)

Compound 9 was prepared from compound 8 as described in the general method for converting the substituted 2-hydroxy benzoic acid derivatives into their substituted 2-(2-hydroxy-ethoxy)-benzoic acid amides (Example 21). The yield of compound 9 was 81%. The $^1$H-NMR spectrum (300 MHz, CDCl$_3$) of the purified product was: 3.89 (s, 3H), 3.93-3.96 (t, 2H), 4.33-4.36 (t, 2H), 7.08 (s, 1H), 7.62 (s, 1H).

EXAMPLE 30

This example illustrates synthesis of N-[4-(6,7-dimethoxy-3,4-dihydro-1H-isoquinolin-2-yl)-butyl]-2-(2-hydroxy-ethoxy)-5-iodo-3-methoxy-benzamide (compound 4f)

Compound 4f was prepared from 9 and 1b as described in the general method for synthesis of the substituted 2-hydroxybenzoic acid amides (Example 9). The yield of 4f was 29%. The $^1$H-NMR spectrum (300 MHz, CDCl$_3$) of the purified product was: 1.72-1.75 (m, 4H), 2.56 (m, 2H), 2.75-2.77 (m, 2H), 2.81-2.83 (m, 2H), 3.49-3.51 (m, 2H), 3.55 (s, 2H), 3.56-3.60 (t, 2H), 3.82 (s, 3H), 3.83 (s, 3H), 3.85 (s, 3H), 4.06-4.10 (t, 2H), 6.47 (s, 1H), 6.57 (s, 1H), 6.90 (s, 1H), 7.57 (s, 1H), 7.70-7.80 (s, 1H).

EXAMPLE 31

This example illustrates synthesis of 2-(2-(4-(6,7-dimethoxy-3,4-dihydroisoquinolin-2(1H)-yl)butylcarbamoyl)-4-iodo-6-methoxyphenoxy)ethyl methanesulfonate (compound 5f).

Compound 5f was prepared from 4f as described in the general method for converting the substituted 2-hydroxyethoxy benzoic acid amides of the present teachings to their methanesulfonic acid esters (Example 24). The yield of 5f was 61%. The $^1$H-NMR spectrum (300 MHz, CDCl$_3$) of the purified product was: 1.72 (m, 4H), 2.55 (s, 2H), 2.70 (d, 2H), 22.76 (d, 2H), 3.05 (s, 3H), 3.85 (m, 9H), 4.26 (m, 2H), 4.49 (m, 2H), 6.49 (s, 1H), 6.55 (s, 1H), 6.93 (d, 1H), 7.51 (m, 1H), 8.02 (s, 1H). LCMS m/e: 663.20 (M+H). Anal. (C$_{25}$H$_{32}$FIN$_2$O$_5$) C: Calcd, 51.20; found 36.61; C: Calcd, 5.50; found 4.34; N: Calcd, 4.78; found 3.12.

EXAMPLE 32

This example illustrates production of [$^{18}$F]Fluoride.

[$^{18}$F]Fluoride was produced in our institution by proton irradiation of enriched $^{18}$O water (95%) [reaction: $^{18}$O(p, n)$^{18}$F] using either a JSW BC-16/8 (Japan Steel Works) or a CS-15 cyclotron (Cyclotron Corp).

EXAMPLE 33

This example illustrates a general method for labeling the substituted 2-(2-fluoroethoxy)benzoic acid amide analogs with $^{18}$F, in particular [$^{18}$F](N-[4-(6,7-dimethoxy-3,4-dihydro-1H-isoquinolin-2-yl)-butyl]-2-(2-fluoro-ethoxy)-3-methoxy-5-iodo-benzamide (compound [$^{18}$F]3f).

For this synthesis, [$^{18}$F]fluoride (100-150 mCi) was added to a 10-mL Pyrex screw cap tube containing 5-6 mg of Kryptofix 222 and 0.75 mg of K$_2$CO$_3$. Using HPLC grade acetonitrile (3×1.0 mL), the water was azeotropically evaporated from this mixture at 110° C. under a stream of argon. After all of the water was removed, a solution of the precursor, 5f, (1.5-2.0 mg) in DMSO (0.2 mL) was added to the reaction vessel containing the $^{18}$F/Kryptofix mixture. A 3 mm glass bead was added to the reaction vessel to insure a more homogeneous heat distribution when the sample was irradiated with microwaves, and the vessel capped firmly on a specially designed remotely operated capping station. After vortexing, the reaction mixture was irradiated with microwaves for 30-40 sec at medium power (60 Watts) until the thin layer chromatography scanner with a 25% of methanol and 75% dichloromethane mobile phase indicated that the incorporation yield was 40-60%.

After adding 6 mL of water and shaking, the solution was loaded on a C-18 reverse phase Waters Oasis cartridge (HLB-6 cc) that had previously been rinsed with a solution of 5% methanol in water (5-8 mL). The sample was then rinsed 3 times with 6 mL water to eliminate the unreacted fluoride. The retained activity was eluted with 5-8 mL of acetonitrile. After evaporating the acetonitrile to a volume of <0.5 mL, the sample was loaded on a C-18 Alltech econosil semi-preparative HPLC column (250×10 um). The product was eluted with 29% acetonitrile and 71% 0.1M ammonium formate buffer at a flow rate of 4.5 mL/min. The retention time of the [$^{18}$F]3f was ~33 min. The solution containing the [$^{18}$F]3f was concentrated, resuspended in saline, and a 100 uL aliquot sent for quality control analysis before using it in the biodistribution and imaging studies. The entire procedure required ~2 h.

Quality control analysis was performed on an analytical HPLC system that consisted of an Alltech econosil reversed phase C-18 column (250×4.6 mm) with a mobile phase of 35% acetonitrile and 65% 0.1 M ammonium formate buffer at pH 4.0-4.5. At a flow rate of 1.2 mL/min, the [$^{18}$F]3f eluted at 13.2 min with a radiochemical purity of >99%. The labeling yield was ~30% (decay corrected), and the specific activity was >2000 Ci/mmol.

EXAMPLE 34

This example illustrates synthesis of [$^{18}$F](N-[4-(6,7-dimethoxy-3,4-dihydro-1H-isoquinolin-2-yl)-butyl]-2-(2-fluoro-ethoxy)-5-methyl-benzamide (compound [18F]3c).

Compound [$^{18}$F]3c was prepared from 5c as described above for [$^{18}$F]3f with the following exceptions. The semi-preparative HPLC mobile phase was 39% methanol and 61% 0.1 M formate buffer. At a flow rate of 3.5 mL/min, the [$^{18}$F]3c eluted at ~33 min with a radiochemical purity of >99%. The labeling yield was ~35% (decay corrected), and the specific activity was >1500 Ci/mmol. The entire procedure took ~2 h.

To check that the chemical characteristics of [$^{18}$F]3c were identical to the cold standard, 3c, both compounds were run on the analytical HPLC system with a mobile phase of 52% methanol and 48% 0.1 M formate buffer. At a flow rate of 1.5 mL/min, the two compounds co-eluted with a retention time of 4.7 min.

EXAMPLE 35

This example illustrates synthesis of [$^{18}$F](N-[4-(6,7-dimethoxy-3,4-dihydro-1H-isoquinolin-2-yl)-butyl]-2-(2-fluoro-ethoxy)-5-bromo-benzamide (compound [$^{18}$F]3d).

Compound [$^{18}$F]3d was prepared from 5d as described above for [$^{18}$F]3f with the following exceptions. The semi-preparative HPLC mobile phase was 13% of THF and 87% 0.1 M formate buffer. At a flow rate of 3.5 mL/min, the

[$^{18}$F]3d eluted at ~20 min with a radiochemical purity of >98%. The labeling yield was ~30% (decay corrected), and the specific activity was >1500 Ci/mmol. The entire procedure took ~2 h.

To check that the chemical characteristics of [$^{18}$F]3d were identical to the cold standard, 3d, both compounds were run on the analytical HPLC system with a mobile phase of 38% acetonitile and 62% 0.1 M formate buffer. At a flow rate of 1.5 mL/min, the two compounds co-eluted with a retention time of ~8 min.

EXAMPLE 36

This example illustrates synthesis of [$^{18}$F](N-[4-(6,7-dimethoxy-3,4-dihydro-1H-isoquinolin-2-yl)-butyl]-2-(2-fluoro-ethoxy)-5-Iodo-benzamide (compound [$^{18}$F]3e).

Compound [$^{18}$F]3e was prepared from 5e as described above for [$^{18}$F]3f with the following exceptions. The semi-preparative HPLC mobile phase was 15% THF and 85% 0.1 M formate buffer. At a flow rate of 6.0 mL/min, the [$^{18}$F]3e eluted at ~35 min with a radiochemical purity of >99%. The labeling yield was ~30% (decay corrected), and the specific activity was >1500 Ci/mmol. The entire procedure took ~2 h.

To check that the chemical characteristics of [$^{18}$F]3e were identical to the cold standard, 3e, both compounds were run on the analytical HPLC system with a mobile phase of 13% acetonitrile and 87% 0.1 M formate buffer. At a flow rate of 2.0 mL/min, the two compounds co-eluted with a retention time of 15.2 min.

EXAMPLE 37

This example provides an elemental analysis of various compounds of the present teachings. The data are presented in Table V.

TABLE V

| | | Calculated | | | Measured | | |
|---|---|---|---|---|---|---|---|
| Compounds | Formula | C | H | N | C | H | N |
| 2d | $C_{22}H_{27}BrN_2O_4 \cdot 1.25H_2O$ | 54.38 | 6.12 | 5.77 | 54.44 | 5.74 | 5.69 |
| 2e | $C_{22}H_{27}IN_2O_4 \cdot 0.75H_2O$ | 50.44 | 5.48 | 5.35 | 50.45 | 5.27 | 5.24 |
| 5c | $C_{26}H_{36}N_2O_7S$ | 59.98 | 6.97 | 5.38 | 59.89 | 6.94 | 5.49 |
| 3a | $C_{23}H_{30}ClFN_2O_4 \cdot H_2O$ | 58.66 | 6.85 | 5.95 | 58.94 | 6.65 | 6.01 |
| 3b | $C_{26}H_{33}BrFN_2O_7 \cdot 0.5H_2O$ | 52.62 | 5.77 | 4.72 | 53.29 | 6.27 | 3.98 |
| 3c | $C_{26}H_{34}FN_2O_6 \cdot H_2O$ | 61.52 | 7.15 | 5.52 | 61.84 | 6.95 | 5.27 |
| 3d | $C_{25}H_{31}BrFN_2O_6 \cdot 1.5H_2O$ | 51.64 | 5.89 | 4.82 | 51.32 | 5.47 | 4.59 |
| 3e | $C_{25}H_{31}FIN_2O_6 \cdot 1.75H_2O$ | 47.44 | 5.49 | 4.43 | 47.07 | 5.09 | 4.11 |

EXAMPLE 38

Figure 9:
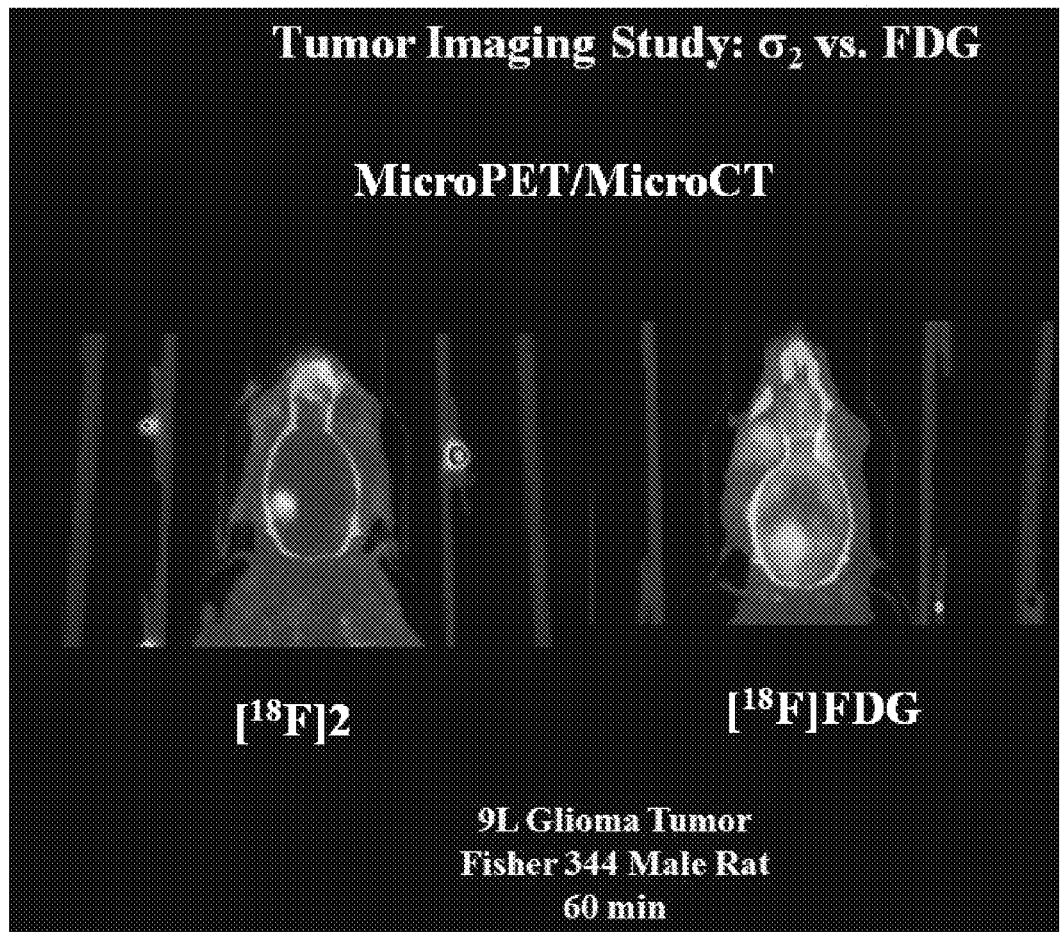
FIG. 9 illustrates an image of a glioma using [$^{18}$F]3f of the present teachings compared to [$^{18}$F]FDG.

This example illustrates, in FIG. 9 (Tumor Imaging Study: $\sigma_2$ vs. FDG), imaging of a glioma using [$^{18}$F]3f of the present teachings compared to [$^{18}$F]FDG. Note greater contrast using compound [$^{18}$F]3f as a radiotracer.

Patents and publications discussed herein are hereby incorporated by reference.

What is claimed is:

1. A method of imaging a tumor in a mammal, the method comprising:
administering to the mammal a radiolabelled fluoro-alkoxybenzamide compound of structure

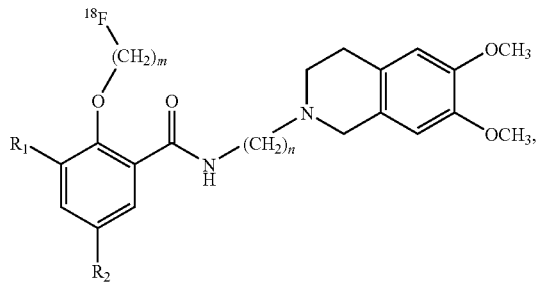

wherein m is an integer from 1 to about 10, n is an integer from 1 to about 10, and $R_1$ and $R_2$ are each independently selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$, or a salt thereof; and
subjecting the mammal to positron emission tomography (PET) scanning.

2. A method of imaging a tumor in accordance with claim 1, wherein m=2, n=4, $R_1$ is selected from the group consisting of H and $OCH_3$, and $R_2$ is selected from the group consisting of $CH_3$, Br and I.

3. A method of imaging a tumor in accordance with claim 1, wherein m=2, n=4, $R_1$ is H, and $R_2$ is $CH_3$.

4. A method of imaging a tumor in accordance with claim 1, wherein m=2, n=4, $R_1$ is H, and $R_2$ is Br.

5. A method of imaging a tumor in accordance with claim 1, wherein m=2, n=4, $R_1$ is H, and $R_2$ is I.

6. A method of imaging a tumor in accordance with claim 1, wherein m=2, n=4, $R_1$ is $OCH_3$, and $R_2$ is I.

7. A method of imaging a solid tumor in a mammal, the method comprising:
administering to the mammal a radiolabelled fluoro-alkoxybenzamide compound of structure

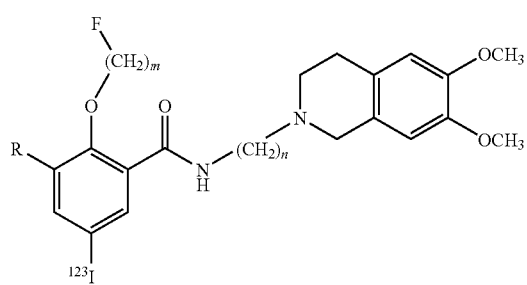

wherein m is an integer from 1 to about 10, n is an integer from 1 to about 10, and R is selected from the group consisting of H, a halogen selected from the group consisting of I, Br, Cl and F, a $C_{1-4}$ alkoxy, a $C_{1-4}$ alkyl, a $C_{1-4}$ fluoroalkyl, a $C_{1-4}$ fluoroalkoxy, $CF_3$, $OCF_3$, $SCH_3$, $SCF_3$, and $NH_2$, or a salt thereof; and subjecting the mammal to single photon emission computed tomography (SPECT) imaging.

8. A method in accordance with claim 7, wherein m=2, n=4 and R is selected from the group consisting of H and methoxy.

* * * * *

UNITED STATES PATENT AND TRADEMARK OFFICE
CERTIFICATE OF CORRECTION

PATENT NO. : 7,947,838 B2                                                Page 1 of 1
APPLICATION NO. : 12/643175
DATED : May 24, 2011
INVENTOR(S) : Robert Mach and Zhude Tu It is certified that error appears in the above-identified patent and that said Letters Patent is hereby corrected as shown below:

Column 10, lines 56 to 57, the text reading "$^{18}$F-labeled PET [$^{18}$F]3c, [$^{18}$F]3d, probes" should read -- $^{18}$F-labeled PET probes--

Column 13, lines 43, the text reading "($\sigma_2$; $\sigma_1$" should read --$\sigma_2$: $\sigma_1$--

Column 22, line 45 and column 24, line 2, the portion of the text reading "110°C." should read --110°C--

Column 24, lines 43, the text reading "compound [18F]3c" should read --compound [$^{18}$F]3c--

Signed and Sealed this
Fifth Day of July, 2011

David J. Kappos
*Director of the United States Patent and Trademark Office*